US007857806B2

(12) United States Patent
Karpowicz et al.

(10) Patent No.: US 7,857,806 B2
(45) Date of Patent: *Dec. 28, 2010

(54) PUMP SYSTEM FOR NEGATIVE PRESSURE WOUND THERAPY

(75) Inventors: John Karpowicz, Chester Springs, PA (US); Christopher L. Radl, Malvern, PA (US); Kevin P. Klocek, Wynnewood, PA (US); John R. Boehringer, Wynndwood, PA (US); Derek Norton, Pottstown, PA (US); Robert Kropp, Norristown, PA (US)

(73) Assignee: Boehringer Technologies, L.P., Phoenixville, PA (US)

( * ) Notice: Subject to any disclaimer, the term of this patent is extended or adjusted under 35 U.S.C. 154(b) by 23 days.

This patent is subject to a terminal disclaimer.

(21) Appl. No.: 11/786,475

(22) Filed: Apr. 12, 2007

(65) Prior Publication Data
US 2007/0219532 A1    Sep. 20, 2007

Related U.S. Application Data

(63) Continuation-in-part of application No. 11/268,212, filed on Nov. 7, 2005.

(60) Provisional application No. 60/699,218, filed on Jul. 14, 2005, provisional application No. 60/847,221, filed on Sep. 26, 2006, provisional application No. 60/792,187, filed on Apr. 14, 2006.

(51) Int. Cl.
*A61M 1/00* (2006.01)
*A61M 27/00* (2006.01)
*A61F 13/00* (2006.01)
*A61H 7/00* (2006.01)

(52) U.S. Cl. .................... 604/540; 604/541; 604/313; 604/304; 604/305; 601/6

(58) Field of Classification Search .................. 604/35, 604/65–67, 118–119, 245–247, 304, 313, 604/315–327, 355; 601/6; 606/7–14
See application file for complete search history.

(56) References Cited

U.S. PATENT DOCUMENTS 3,042,041 A    7/1962    Jascalevich (Continued)

FOREIGN PATENT DOCUMENTS

EP    0853950 A1    8/1995

(Continued)

OTHER PUBLICATIONS

The International Search Report and Written Opinion dated Mar. 24, 2008.
KCI (The Clinical Advantage), Info V.A.C. User Manuel, literature, Dec. 2006.

(Continued)

*Primary Examiner*—Tatyana Zalukaeva
*Assistant Examiner*—Susan Su
(74) *Attorney, Agent, or Firm*—Caesar, Rivise, Bernstein, Cohen & Pokotilow, Ltd.

(57) ABSTRACT

A pump system for applying negative pressure to a wound, including a flow monitor capable of detecting a deviation from a reference airflow rate provided by a controlled leak to determine whether the system is operating normally or abnormally, and a flow status annunciator to indicate a normal operating condition or whether an abnormal condition is a leak or an occluded line in the system. The pump system further includes a pressure controller for regulating operation of a pump to control pressure in the system at a range around a user-selected setpoint. The pump system may also include a waste collector and a level sensor for detecting when the collector is full.

9 Claims, 12 Drawing Sheets

U.S. PATENT DOCUMENTS

| | | | |
|---|---|---|---|
| 3,397,648 A | 8/1968 | Henderson | |
| 3,568,675 A | 3/1971 | Harvey | |
| 3,599,639 A | 8/1971 | Spotz | |
| RE28,405 E | 5/1975 | Sollerud | |
| 4,180,074 A | 12/1979 | Murry et al. | |
| 4,231,375 A | 11/1980 | Boehringer et al. | |
| 4,257,437 A * | 3/1981 | Pearson | 137/8 |
| 4,341,235 A * | 7/1982 | Nord | 137/312 |
| 4,385,630 A | 5/1983 | Gilcher et al. | |
| 4,453,937 A | 6/1984 | Kurtz et al. | |
| 4,710,165 A | 12/1987 | McNeil et al. | |
| 4,797,666 A * | 1/1989 | Baxter et al. | 340/606 |
| 4,930,997 A | 6/1990 | Bennett | |
| 4,969,880 A | 11/1990 | Zamierowski | |
| 4,971,034 A | 11/1990 | Doi et al. | 128/6 |
| 5,047,072 A | 9/1991 | Wertz et al. | |
| 5,092,858 A | 3/1992 | Benson et al. | |
| 5,380,308 A | 1/1995 | Gunya et al. | |
| 5,448,177 A * | 9/1995 | Thompson | 324/557 |
| 5,549,584 A | 8/1996 | Gross | |
| 5,636,643 A | 6/1997 | Argenta et al. | |
| 5,755,884 A * | 5/1998 | Buckler et al. | 118/317 |
| 5,836,909 A * | 11/1998 | Cosmescu | 604/35 |
| 6,045,541 A | 4/2000 | Matsumoto et al. | |
| 6,071,267 A | 6/2000 | Zamierowski | |
| 6,142,982 A | 11/2000 | Hunt et al. | |
| 6,159,180 A * | 12/2000 | Kriesel et al. | 604/132 |
| 6,183,441 B1 * | 2/2001 | Kriesel et al. | 604/132 |
| 6,458,109 B1 | 10/2002 | Henley et al. | |
| 6,533,757 B1 | 3/2003 | Lampropoulos et al. | |
| 6,557,704 B1 | 5/2003 | Randolph | |
| 6,599,277 B2 | 7/2003 | Neubert | |
| 6,648,862 B2 | 11/2003 | Watson | |
| 6,685,681 B2 | 2/2004 | Lockwood et al. | |
| 6,695,823 B1 | 2/2004 | Lina et al. | |
| 6,695,824 B2 | 2/2004 | Howard et al. | |
| 6,755,807 B2 | 6/2004 | Risk et al. | |
| 6,764,462 B2 | 7/2004 | Risk et al. | |
| 6,960,190 B2 | 11/2005 | Stinson | |
| 7,004,915 B2 | 2/2006 | Boynton et al. | |
| 7,128,727 B2 * | 10/2006 | Flaherty et al. | 604/131 |
| 7,128,735 B2 | 10/2006 | Weston | |
| 7,144,390 B1 | 12/2006 | Hannigan et al. | |
| 7,195,624 B2 | 3/2007 | Lockwood et al. | |
| 7,438,705 B2 | 10/2008 | Karpowicz et al. | |
| 7,570,997 B2 | 8/2009 | Lovett et al. | |
| 2002/0161317 A1 | 10/2002 | Risk et al. | |
| 2002/0188279 A1 * | 12/2002 | Waddell et al. | 604/540 |
| 2002/0198503 A1 | 12/2002 | Risk, Jr. et al. | |
| 2002/0198504 A1 * | 12/2002 | Risk et al. | 604/318 |
| 2003/0014022 A1 | 1/2003 | Lockwood et al. | |
| 2003/0040687 A1 | 2/2003 | Boynton et al. | 601/6 |
| 2003/0093041 A1 | 5/2003 | Risk et al. | |
| 2003/0098854 A1 | 5/2003 | Laliberte | |
| 2004/0002670 A1 | 1/2004 | Mothersbaugh et al. | |
| 2004/0006319 A1 | 1/2004 | Lina et al. | |
| 2004/0024361 A1 * | 2/2004 | Fago et al. | 604/152 |
| 2004/0054338 A1 | 3/2004 | Bybordi et al. | |
| 2004/0064132 A1 | 4/2004 | Boehringer et al. | |
| 2004/0208756 A1 | 10/2004 | Adahan | |
| 2005/0004534 A1 | 1/2005 | Lockwood et al. | |
| 2005/0124966 A1 | 6/2005 | Karpowicz et al. | |
| 2005/0209574 A1 | 9/2005 | Boehringer et al. | |
| 2005/0215961 A1 | 9/2005 | Romano et al. | |
| 2005/0228329 A1 | 10/2005 | Boehringer et al. | |
| 2005/0279169 A1 * | 12/2005 | Lander | 73/592 |
| 2005/0287007 A1 | 12/2005 | Leonhard | |
| 2006/0025727 A1 | 2/2006 | Boehringer et al. | |
| 2006/0027267 A1 * | 2/2006 | Fritze | 137/487.5 |
| 2006/0036221 A1 * | 2/2006 | Watson, Jr. | 604/319 |
| 2006/0129137 A1 | 6/2006 | Lockwood et al. | |
| 2006/0196505 A1 | 9/2006 | Izuchukwu | 128/203.15 |
| 2007/0032754 A1 | 2/2007 | Walsh et al. | |
| 2007/0032755 A1 | 2/2007 | Walsh et al. | |
| 2007/0167927 A1 | 7/2007 | Hunt et al. | |
| 2008/0004549 A1 | 1/2008 | Anderson et al. | |
| 2008/0071161 A1 | 3/2008 | Joeb et al. | |
| 2008/0071162 A1 | 3/2008 | Joeb et al. | |
| 2008/0071214 A1 | 3/2008 | Locke et al. | |
| 2008/0071216 A1 | 3/2008 | Locke et al. | |
| 2008/0071234 A1 | 3/2008 | Kelch et al. | |
| 2008/0071235 A1 | 3/2008 | Locke et al. | |
| 2008/0077078 A1 | 3/2008 | Locke et al. | |
| 2008/0140029 A1 | 6/2008 | Smith et al. | |
| 2008/0228526 A1 | 9/2008 | Locke et al. | |

FOREIGN PATENT DOCUMENTS

| | | |
|---|---|---|
| EP | 0777504 B1 | 10/1998 |
| WO | WO 96/05873 | 2/1996 |
| WO | WO 97/18007 | 5/1997 |
| WO | 0021586 | 4/2000 |
| WO | 0134223 | 5/2001 |
| WO | 01037922 A3 | 5/2001 |
| WO | 02092783 A2 | 11/2002 |
| WO | WO 03/016719 | 2/2003 |
| WO | 03/057070 A2 | 7/2003 |
| WO | WO 2007/013049 | 2/2007 |
| WO | WO 2007/013064 | 2/2007 |
| WO | 2007030601 A2 | 3/2007 |
| WO | 2007041642 A2 | 4/2007 |
| WO | 2008012278 A1 | 1/2008 |
| WO | 2008021306 A2 | 2/2008 |
| WO | 2008/039223 A1 | 4/2008 |
| WO | 2008/039314 A2 | 4/2008 |
| WO | 2008040020 A2 | 4/2008 |
| WO | 2009021047 A2 | 2/2009 |

OTHER PUBLICATIONS

Argenta et al., "Vacuum-Assisted Closure: A New Method for Wound Control and Treatment: Clinical Experience", Article, Annals of Plastic Surgery, No. 6, 38:563-577, Jun. 1977.

The Engineering ToolBox: Positive Displacement Pumps, literature, website: http://www,engineeringtoolbox.com Sep. 15, 2008.

Blue Sky Medical, Vista Versatile 1 Portable, 20 sheets, website: http://www.blueskymedical.com Feb. 29, 2008.

Michael S. Miller, DO., et al., BioMechanics, "Negative Pressure Wound Therapy Options Promote Patient Care," article, Sep. 2005.

V.A.C., Instill, Dual Therapies, "One Advanced Wound Healing System," KCI brochure 2006.

KCI, V.A.C., Instill, Recommended Guidelines, brochure, Aug. 2004.

KCI, V.A.C. Therapy Wound Reference, No. 4 series, Orthopedic Trauma Wounds, brochure, 2005, 2006.

KCI, V.A.C. Therapy Clinical Guidelines, manual, Jul. 2007.

* cited by examiner

PUMP SYSTEM FOR NEGATIVE PRESSURE WOUND THERAPY

REFERENCE TO RELATED APPLICATIONS

This application is a continuation in part of U.S. patent application Ser. No. 11/268,212 which was filed on Nov. 7, 2005 and which claims priority of U.S. Provisional Application No. 60/699,218, filed Jul. 14, 2005. This application also claims priority of U.S. Provisional Application No. 60/792,187 filed Apr. 14, 2006, and of U.S. Provisional Application No. 60/847,221, filed Sep. 26, 2006.

FIELD OF THE INVENTION

The invention relates to the general field of wound treatment, and to the more specific field of devices for wound drainage and treatment with suction.

BACKGROUND OF THE INVENTION

It is well known to treat wounds by applying suction under airtight wound covers. The suction can be used to aspirate wound exudate and other liquids from the wound and/or the wound packing materials, and the suction can be applied as a healing modality for its well known antiseptic and tissue regeneration effects.

A primary concern in using suction assisted wound therapy is maintaining consistent suction pressure at the wound. It is increasingly recognized that once suction wound dressings are applied, the suction should be maintained at certain levels. Loss of suction to the wound can result if leaks or blockages occur in the system.

Leaks can occur through breach of the airtight seals surrounding the wound. The earliest devices merely ran a tube under the edge of a wound cover and applied an adhesive or paste around the tube and cover to maintain an airtight seal. The other end of the tube was connectable to a waste collection reservoir and suction regulator of a hospital suction system, and the pressure selected at the regulator was assumed to be the approximate pressure communicated to the wound area under the cover. The test for leakage was visual observance of the cover contracting and the absence of whistling noise when negative pressure was applied. See, e.g., M. E. Chariker, et al, "Effective Management of Incisional and Cutaneous Fistulae with Closed Suction Wound Drainage", *Contemporary Surgery*, vol. 34, June 1989, pages 59-63. This initial check for an airtight seal did not, however, provide any warning if the system developed a leak or if blockage occurred in the collection circuit after hours of use.

The adhesive seal around the suction tube or other tubes which run under the edge of the wound cover in these prior wound dressings is vulnerable to cracking and breaching the airtight seal, creating air leakage into the cover. Improvements have been made to suction wound therapy devices to reduce the likelihood of leakage. For example, U.S. patent application Ser. No. 11/181,128, filed Jul. 14, 2005 and commonly assigned with this application, discloses a tube attachment patch to allow the suction tube to be terminated outside of the primary cover and thus reduce the risk of breaking the adhesive seal to the skin. While these newer tube attachment devices provide more seal integrity, there is still the potential for breach of the airtight seals due to external causes such as patient movement in bed.

Blockage of suction to the wound can occur for several reasons. A waste collector for wound exudate is usually positioned somewhere in the suction line between the wound and the suction source. Waste collectors incorporate shut-off mechanisms that will shut off suction to the wound when the collector is overfilled. Another potential blockage is kinking or crimping of the suction line itself. Other potential blockage causes may be debris from the wound, clotting, or drying of wound exudates (particularly where the volume of wound exudates is small relative to the reference airflow). The suction source may also be inadvertently turned off, a line may be inadvertently clamped, or the suction regulator may be misadjusted after the dressing is applied. Since suction wound dressings are intended to last for long periods without changing, usually 24 hours or greater, a leak or blockage could develop unnoticed and not be detected for a duration sufficient to negate the beneficial healing effect of suction as well as increase the risk of infection. There are currently devices to sense when a waste collector canister is filled and provide a warning signal to empty it. None of the devices, however, provides a comprehensive and reliable monitoring of system operation, nor cover the full range of fault possibilities with leakage or blockage.

In their efforts to improve over these prior art devices, the present inventors designed a suction wound dressing monitoring system as described in U.S. patent application Ser. No. 11/268,212. In doing so, they consider the impracticality of locating expensive pressure transducers in any of the system components that should be single-use disposable items due to contamination by body fluids. The designers considered that the same basic system should preferably be effective in detecting and indicating both leaks and system blockage, and that the detection of leaks or blockage should preferably be effective regardless where the leak or blockage occurs in the system. They considered that the system should preferably provide clear visual indication of both normal and abnormal operation, and could usefully provide aural indication and auto-recording of abnormalities. They also considered that the suction monitoring capability should be easily convertible from use with a stationary suction system, as typically found in hospital care rooms, to use with a portable suction pump.

The inventors considered that particularly when using a stationary suction source, it would be advantageous for the monitoring system to include an air dryer or dehumidifier to remove moisture from the air suctioned from the wound. Often, the air within the system is saturated with moisture (i.e., 100% relative humidity) such that formation of water droplets due to condensation is common and likely. However, such water droplets can potentially interfere with the proper functioning of a flow monitor in the system, and may further increase the likelihood of contamination in the system. Accordingly, a dehumidifier to reduce the humidity of the air would prevent the formation of water droplets and improve the functioning of the system and help to prevent contamination.

Conversely, the inventors considered that at other times, the system is not saturated and drying of wound exudates may occur in the system conduit, causing or aggravating blockages. Therefore, in some circumstances, it may be advantageous to humidify the air being suctioned from the wound.

In addition, the inventors have considered that when using a portable pump as the suction source it would be advantageous to use an electronic flow monitor in the monitoring system to detect deviation from a reference airflow and to provide corresponding indicators and/or alarms. An embodiment of the electronic flow monitor could be a microprocessor that is further capable of other useful functions, such as recording and accumulating various parameters in time units and providing reports of such time records.

For safety and redundancy, the inventors considered that it would be advantageous to provide the pump with a pressure controller that is independent of the flow monitor such that the pump can control pressure to a user-selected pressure setpoint without the need to receive or rely on a signal from the flow monitor. However, the pressure controller could provide to the flow monitor data related to pump operation, such as the detection of a faulty pressure transducer or a runaway pump condition. Moreover, a signal from the flow monitor could be used to periodically or temporarily reset the pressure setpoint for the pressure controller to a second pressure lower or higher than the selected pressure, such as for intermittent operation or to create a line clearing pressure pulse if a fluid flow deviation begins to indicate a conduit occlusion.

The inventors considered that it would be useful for the flow monitor to be coupled to an annunciator on the pump unit, the annunciator including visual and/or auditory indicators, for convenient indication of status conditions related to fluid flow, such as: normal operation, low level leak, high level leak, line occlusion, and filled waste collector, as well as an indication of patient compliant use. They also considered that it would be useful for the pump to have a separate error indicator for convenient indication of error conditions that are not related to fluid flow such as overpressure detection by the pressure transducer, pressure transducer failure, waste collector canister not attached, low battery voltage, attachment of incorrect power supply, low operating time remaining, collection canister full, and pump motor not operational.

Although the waste collector could be located anywhere between the wound dressing and the vacuum source, the inventors considered that when using a portable pump vacuum source, it would be advantageous for the pump unit to provide a docking station for the waste collector, such that the collector canister can be securely attached to the pump unit. In that configuration, the pump unit may also include a level detector for detecting and indicating the fill status of the waste collector. For example, the pump unit may have a level sensor, such as a capacitance sensor, to detect a filled waste collector based upon indications other than pressure differential across a hydrophobic membrane in the collector. If so, the level detector signal may be moderated by an algorithm in the flow monitor to reduce the likelihood of false indications of a full collector caused by sloshing when the pump unit with the waste collector is moved.

BRIEF SUMMARY OF THE INVENTION

The invention provides a wound treatment system for applying negative pressure or suction therapy to a wound. A reference airflow rate is used for monitoring system operation. The negative pressure wound treatment system includes an airtight wound dressing and a suction conduit having one end operatively associated with the wound dressing to communicate suction to the wound and an opposite end operatively connected with a source of suction. The system preferably includes a waste collector disposed in the suction conduit between the wound dressing and the source of suction for collecting fluids aspirated from the wound. The waste collector may have a residual suction capacity to draw fluid through the conduit when the suction source is shut down. The invention provides a reference airflow rate (or "controlled leak") to the suction source when the system is in operation, such that deviation from the reference airflow can be detected as an indication of a change in operation.

In a preferred embodiment of the invention, a portable pump unit is used as the suction source. The pump unit has a flow monitor to monitor airflow through the conduit from the wound dressing to the pump as indicative of the level of negative pressure applied to the wound. Deviation from the reference airflow rate can be used as an indication of an abnormal condition such as leakage of the wound dressing or occlusion in the conduit. The flow monitor may be controlled by a microprocessor or by solid state circuitry capable of also providing additional functions including indicating system status and system errors, and further tracking and reporting time histories of system operation. To compensate for variations in the pump volumetric efficiency at a selected setpoint pressure, the flow monitor can have a look-up table to correlate between measured and actual flow rates for a range of negative pressures.

For safety and redundancy, the pump unit has a pressure transducer and a pressure controller that can operate independently from the flow monitor. The pressure controller may use solid state circuitry or may be controlled by a microprocessor or may be a simple mechanical-type device. A user-operable pressure selector enables a user to select a negative pressure pump output within a range of negative pressure setpoints. The pressure controller controls the operation of the pump to maintain the pressure sensed by the pressure transducer between upper and lower limits around the selected setpoint pressure.

The flow monitor provides signals to an annunciator including a flow indicator, preferably a bar meter that is color coded and gradated to provide a visual indication of fluid flow through the pump, and hence through the system conduit. The annunciator indicates when the air flow through the pump is within a range of the reference airflow that is associated with normal system operation, and conversely indicates when a deviation from the reference airflow is associated with an abnormal operation. Compliant time (i.e., the time during which system operation is normal) is accumulated so that the caregiver can make reasonable assessments as to the effectiveness of the therapy.

The pump also includes an error detector and an error indicator for displaying a visual warning of system errors that are not associated with a deviation of the flow rate through the pump from the reference airflow. Such errors may include overpressure detection by the pressure transducer, pressure transducer failure, waste collector canister not attached, low battery voltage, attachment of incorrect power supply, low operating time remaining, collection canister full, and pump motor not operational. The error detector and error indicator are preferably controlled by a microprocessor or by solid state circuitry, although other mechanisms may be used to control error detection and indication.

Although the pressure controller may operate independently to maintain the setpoint pressure, a therapy timing controller or the flow monitor can be used to reset the pressure setpoint. For example, the therapy timing controller may periodically reset the pressure setpoint between a higher selected pressure and a second lower pressure when intermittent pressure therapy is desired. For another example, the flow monitor may temporarily increase the setpoint pressure when a deviation from the reference airflow rate begins to indicate an occlusion, such that pressure controller causes the pump to start or to increase in speed, creating a vacuum pressure pulse capable of clearing the conduit between the wound dressing and the waste collector.

The pump may also include a timing subsystem to record and accumulate the time units based upon inputs from other sensors, and to provide reports of the time units that the pump is running. The reports may include a record of runtime intervals, a record of the date and duration of runtime intervals, a record of total accumulated runtime, a record of accumulated compliant runtime, and a record of runtime remaining on a preset runtime period.

Various waste collectors may be constructed for collecting wound exudates under negative pressure conditions, including, for example, a flexible bag having an internal support. A preferred waste collector is a disposable upright cylindrical transparent plastic canister with fill level markings on an outside surface. The waste collector canister may be prevented from overfilling by a hydrophobic membrane filter at the top of the canister that shuts off the air flow when the canister is full. The liquids aspirated from the wound may be turned into a gel, for ease of disposal and to prevent spilling, by a gelling agent in the disposable canister. To keep the waste in the canister level, the gelling agent is preferably provided in stacked disks. The waste collector has an inlet connector for a suction tube coming from the wound dressing, and an outlet connector for connecting to a portable pump, a dehumidifier, or a flow monitor. The outlet connector is preferably a proprietary (non-standard) connector that will not connect directly to the standard appliance fitting of a stationary suction system, to prevent the wound from being subjected to excessive suction if the conduit were to be mistakenly connecting directly to the suction system without pressure regulation.

The pump unit may provide a docking station for the waste collector, such that the collector can be securely attached to the pump. The pump unit preferably has a docking station with a profile conforming to an outer surface of the waste collector and a releasable latch fitting adapted to receive the outlet connector of the waste collector.

The pump unit may have a sensor proximate to the collector docking station for detecting the level of waste in the canister, the level sensor preferably being a capacitance detector. The flow monitor is capable of receiving a signal from the level sensor indicating a full collector canister, and the flow monitor may include an algorithm to be applied to the signal to reduce the likelihood of an erroneous indication of a full canister caused by liquid sloshing inside the canister.

The negative pressure wound therapy system may include a dryer or dehumidifier disposed in the conduit between the waste collector and the suction source, and preferably between the waste collector and the flow monitor, for reducing the tendency of condensate droplets to form in the system.

Some applications may necessitate adding moisture to the wound for therapeutic purposes, to maintain a clear collection conduit, or to prevent drying of wound exudates within the conduit. Moisture in the form of humidity and/or a liquid may be added to the wound via a separate conduit or directly into a calibrated vent.

The pump is preferably a portable battery-powered positive displacement pump in which flow rate is approximately proportional to pump speed, such that the flow rate of the system can be detected indirectly by measuring the motor speed or pump speed. A pressure transducer combined with an algorithm or look-up table may be used to correct motor and pump speed to flow for compressibility effect. Thus a motor speed indicator or tachometer may be the preferred monitoring instrument to provide input to the flow monitor. However, other flow rate monitoring instruments could be used, including but not limited to target meters, rotometers, turbine meters, mass flow meters, differential pressure cells, and hot wire anemometers.

The pump unit may have an activated charcoal air filter disposed at an air discharge port of the pump for reducing odors emanating from the pump. The filter may also include a desiccant. The pump may utilize a controlled backpressure to lessen the noise inherent in the operation of the check valves in a positive displacement pump, such as a leaf spring sound damper disposed over the pump outlet.

In a preferred embodiment, a calibrated vent in the suction conduit or tube near the wound dressing establishes the reference airflow by effectively providing a controlled leak rate. The calibrated vent may include, but is not limited to, an orifice, a needle valve, or a sintered porous element. Preferably the vent is located in the tube just outside of the wound cover. The vent may be an aperture in the tube sealed with a porous material having specific flow rate characteristics. The reference airflow rate may be in a preferred range of 50-300 cubic centimeters per minute (cc/min). Higher flows such as 1000 cc/min are possible, but practical limitations on the capacity of the suction source and line losses inherent in small diameter tubing, as well as the ability to detect the typical magnitude of a leak in the wound dressing, suggest that is preferable to use a flow below 1000 cc/min.

By locating the vent in the conduit close to the wound dressing, the reference airflow also serves to purge the conduit of fluids and other wound exudates. The purging effect minimizes the likelihood of reflux of contaminated fluid back into the wound, and the risk of infection attendant to such reflux. Since the fluid does not reside in the conduit for an extended time, the purge effect also reduces the likelihood of blood clotting in the line. The pump system may also provide a pressure pulse generator to clear the collection line of serial slugs of fluid if a reduction in flow is detected.

Although the term "airflow" is used herein for consistency, it should be apparent that it is not limited to the composition of ambient air. It is common in medical settings to alter the composition of airflow to a wound, such as by increased oxygen or therapeutic aerosols or other beneficial medications. It is also understood that in addition to air, the suction source will draw wound exudates and bodily fluids through the suction conduit. The flow of any of these mixed gases or aerosol suspensions, any of which may include wound exudates, should be considered airflow for purpose of this description. The term "fluid flow" is sometimes used interchangeably with "airflow" to more generally indicate a flow of air, possibly including liquid exudates, in the system.

These and other advantages and aspects of the invention will become apparent upon reading the detailed description and drawings that follow.

DETAILED DESCRIPTION OF THE INVENTION

Figure 1:
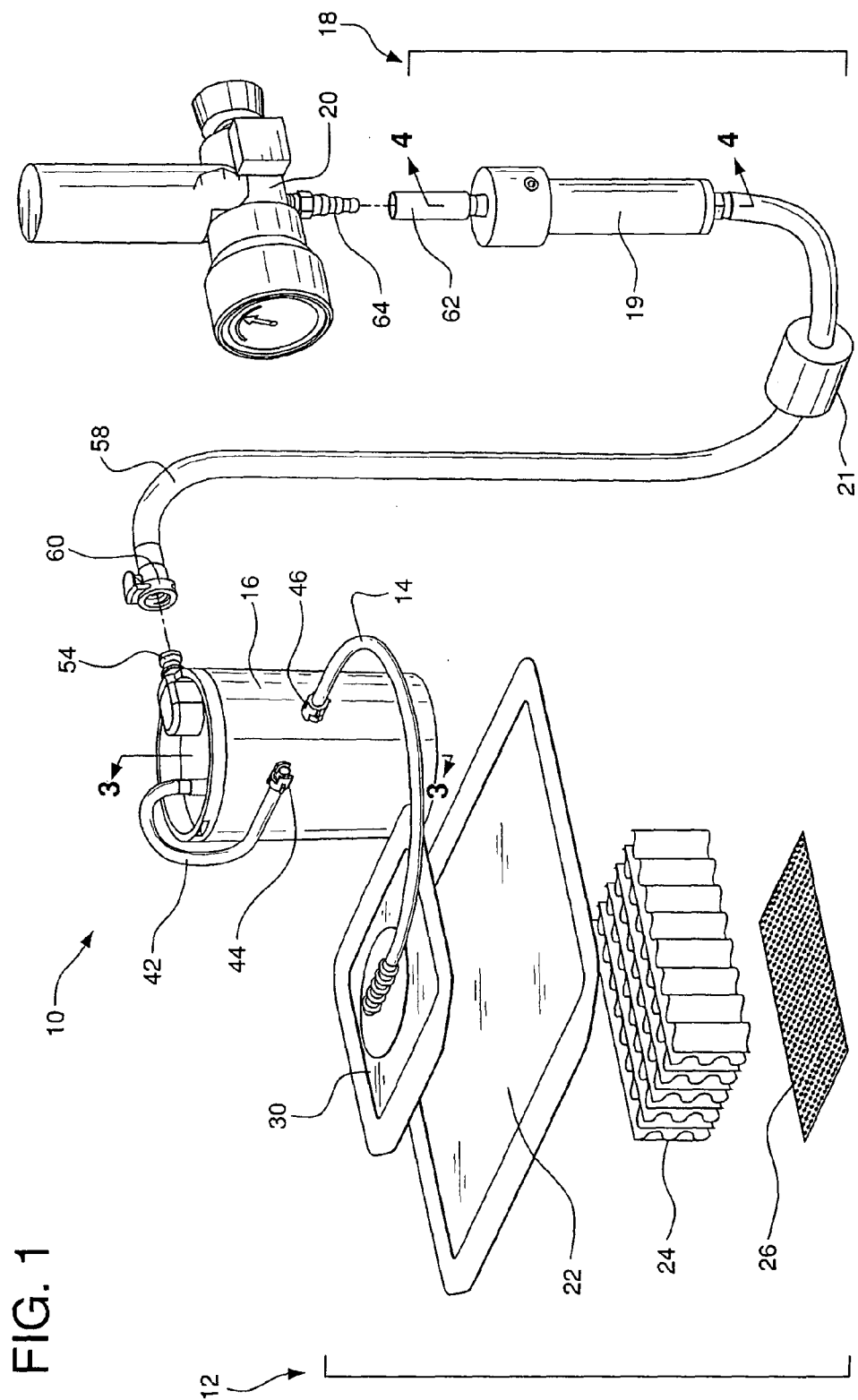
FIG. 1 is an exploded prospective view of an embodiment of a system for negative pressure wound therapy.
Figure 5A:
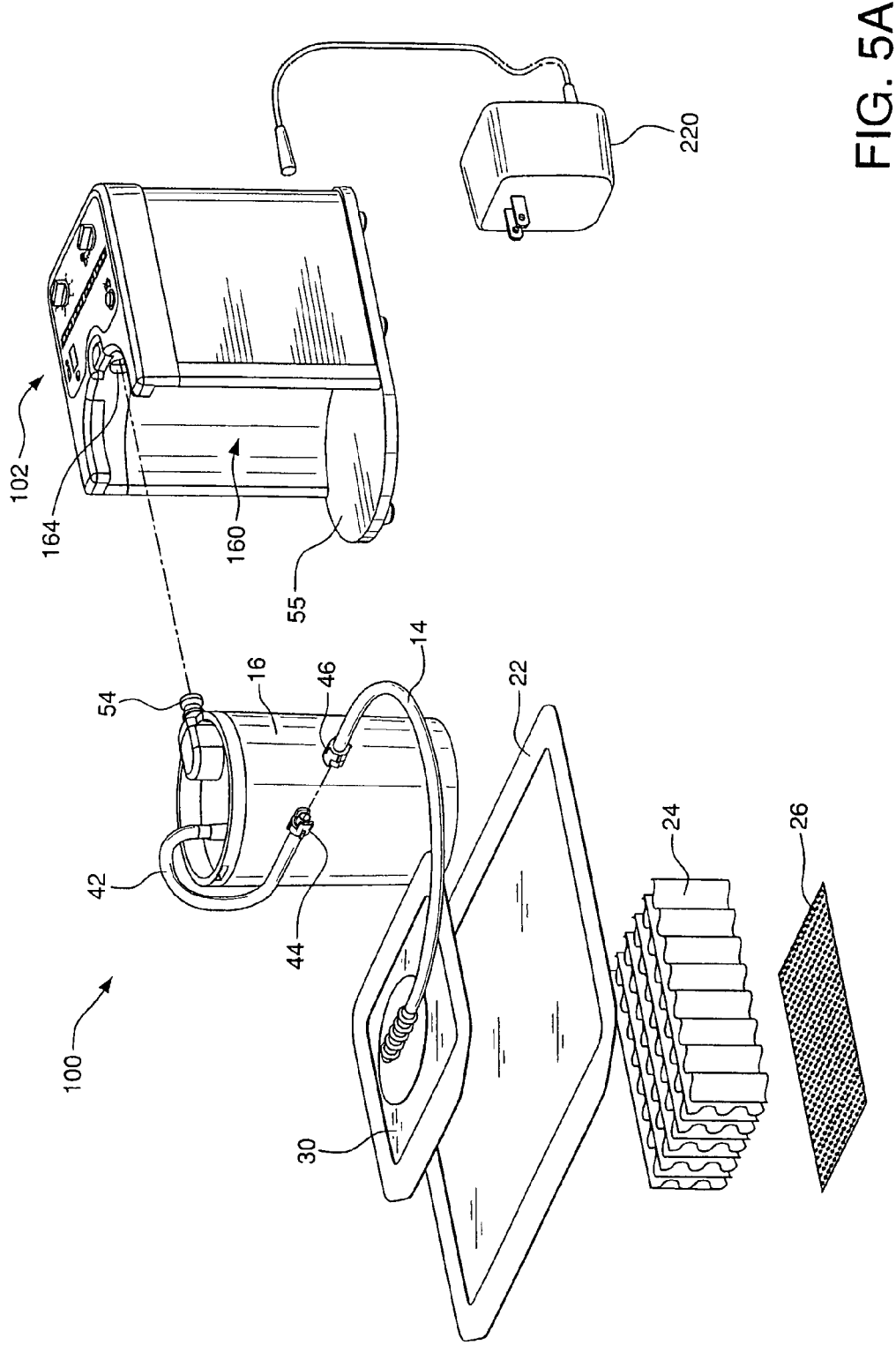
FIG. 5A is an enlarged perspective view of a preferred embodiment of a system for negative pressure wound therapy using a portable suction pump.

FIG. 1 shows an embodiment of a system (10) for negative pressure (suction) wound therapy. The system (10) includes a wound dressing (12), a flow monitoring device (18), and a suction regulator (20) for regulating vacuum from a stationary suction source. FIG. 5A shows an alternate embodiment of a system (10) for negative pressure wound therapy where a portable suction pump unit (102) is used in place of the suction regulator (20) and the stationary suction source.

Wound Dressing

The wound dressing (12) typically includes a primary wound cover (22) and wound packing material (24), and may include a special wound contact layer (26). A suction tube (14) communicates with the wound packing material (24) by running under the edge of the wound cover (22), by extending through the wound cover (22), or by terminating outside of the wound cover (22) and communicating with a nozzle or slot in the wound cover (22). Various wound dressings (12) may be used comprising a wide variety of wound covers (22), wound packing materials (24), optional wound contact layers (26), and means for communicating the suction tube (14) with the packing material (24). The wound dressing (12) shown in the drawings and described herein uses presently preferred components, but the invention is generally applicable to any wound dressing subsystem (12) and is not intended to be limited to any particular components.

The primary wound cover (22) is preferably an airtight wound cover that is vapor permeable. The term "airtight" means that the material is sufficiently occlusive to resist airflow through the cover to maintain suction under the cover while suction is being applied. It is preferred to use a thin film transparent commercial bandage, such as medical grade Tegaderm™ manufactured by 3M, that is impermeable to liquids but permeable to water vapor and oxygen. There are many other thin-film commercial bandages that have similar properties. Highly impermeable materials could also be used. However, since it is beneficial in wound therapy to allow water vapor to escape and oxygen to migrate into the wound, semi-permeable covers of film material such as Tegaderm™ are preferred. In some instances, the primary wound cover (22) could also be a rigid or semi-rigid enclosure placed over the wound. The primary wound cover (22) is generally sealed to the skin surrounding the wound with an adhesive (not shown) incorporated in the wound cover (22), and gap filler paste (not shown) may be used where needed.

Before the wound cover (22) is applied, the wound is generally packed with a wound packing (24). The wound packing (24) may include simple gauze or foam pads or other materials commercially sold as wound packings. The presently preferred wound packing (24) is polyester fibers or comparable resilient fibers in a corrugated layer pattern configured to form a resilient compressible structure, as described in U.S. patent application Ser. No. 10/981,119, commonly assigned with this application.

The wound packing (24) may also be attached to a wound contact layer (26). The presently preferred wound contact layer (26) has a special construction that provides a wound contact surface, with depressions formed into the surface, to work in conjunction with the suction to encourage more rapid tissue regeneration, as described in U.S. patent application Ser. No. 10/982,346, commonly assigned with this application. The contact surface is configured such that voids formed by the depressions remain above the wound surface in the presence of moisture, compressive forces, and suction, thus encouraging local tissue deflection.

Figure 2:
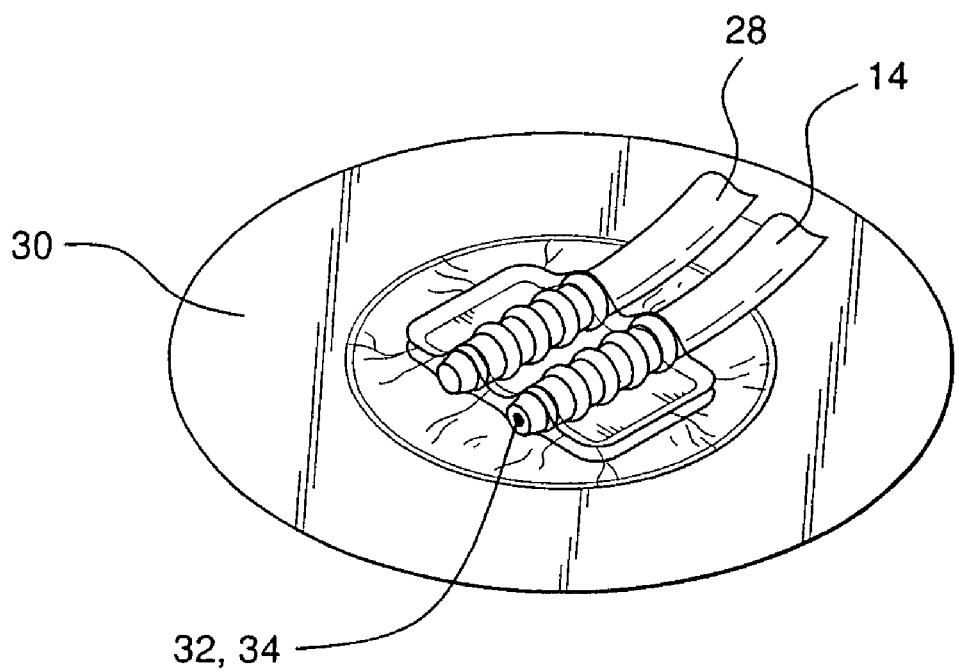
FIG. 2 is a perspective view of a suction tube attachment device showing an air vent in the suction tube to create a controlled reference airflow rate to the suction source.

The wound dressing (12) has a suction tube (14) attached to the wound cover (22), as shown in FIG. 2. The wound dressing (12) may have one or more other tubes (28) for medication supply or wound flushing. The tube(s) (14, 28) may pass through the wound cover (22) or under the edge thereof, but a presently preferred arrangement uses a tube attachment patch (30) to allow the suction tube (14) to be terminated outside of the primary wound cover (12) to reduce the risk of breaking the adhesive seal to the skin, as described in U.S. patent application Ser. No. 11/181,128, commonly assigned with this application.

A distal end of the suction tube (14) in this embodiment has a vent hole (32) that is sealed with a porous plug (34). The porous plug (34) provides a controlled leak, or reference airflow, for flow monitoring devices described hereafter, including the flow monitoring device (18). The vent (32, 34) should be located outside the primary wound cover (22) but is preferably located as close to the wound cover (22) as possible. An advantage of having the suction tube (14) connected to the tube attachment patch (30) outside of the wound cover (22) is that controlled leak reference airflow may be used without drying out the wound, as might occur if the suction tube (14) passed under the wound cover (22) near the wound. While it is feasible to route the suction tube (14) under the wound cover (22) while the controlled leak vent (32, 34) is outside of the actual wound space, it would be important to avoid excessive drying of the wound tissue due to the introduced airflow. In addition, it is possible with the type of tube attachment patch (30) shown in FIG. 2 and described in U.S. patent application Ser. No. 11/181,128 to provide the porous vent (32, 34) as an aperture in the patch (30).

A wound therapist applies the wound dressing (12) to the patient and attaches the system to suction. The therapist remedies leaks in the dressing by smoothing out creases or wrinkles in the wound cover and addressing gaps due to folds in the patient's anatomy. It has at times been useful to address specific areas of difficult anatomy by using a gap filling paste, as is common in ostomy care, such as moldable strip paste from Coloplast. The airflow monitoring instruments described hereafter facilitate the initial dressing set up process by providing active feedback to the therapist on the integrity of the seal around the wound dressing and tubes.

Waste Collector

Figure 3:
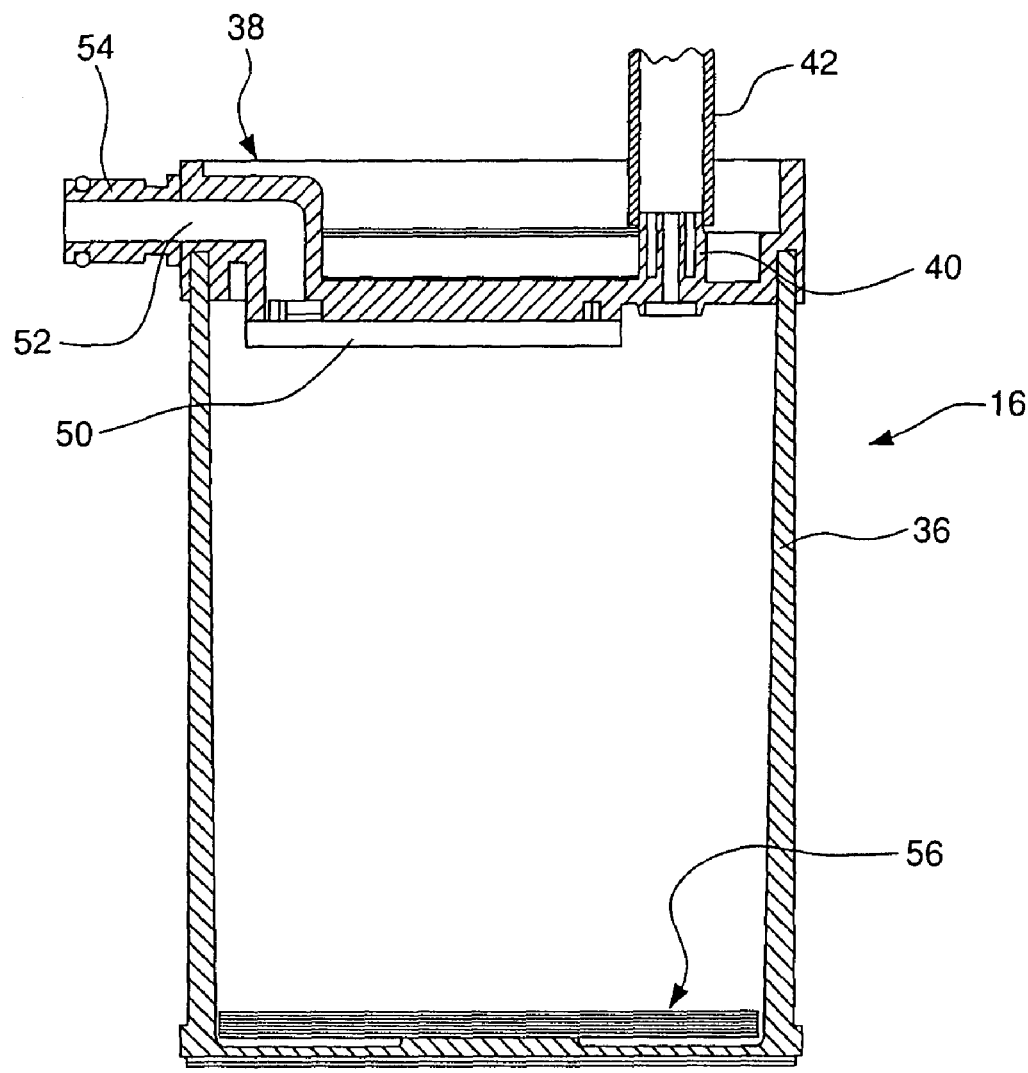
FIG. 3 is a cross-sectional view of a waste collector of FIG. 1, taken through section 3-3, showing the shutoff membrane and gel agents.

Since a primary function of negative pressure or suction therapy is to drain liquids from the wound, a system (10) normally includes a waste collector (16) for collecting fluids aspirated from the wound. As shown in the embodiment of FIG. 1, the air passage through the collector or container (16) forms a part of a suction conduit between the wound and the suction source. As shown in cross-section in FIG. 3, the collector (16) may be an upright canister (36) with a right circular cylinder profile. The canister (36) is preferably made of a transparent or semi-transparent material such as plastic that enables viewing of the level of liquid contained therein. The canister (36) may have fill level markings in a band extending vertically along the outside of the canister. The markings may be on a paper label adhesively glued to the canister (36) or may be marked, embossed, or etched directly onto the canister (36). The fill level markings may also be created on the pump unit (102). The canister (36) is preferably a disposable, single-use device. The canister (36) has a lid (38) incorporating a fitting (40) passing through the lid (38) for the attachment of an inlet tube (42). The inlet tube (42) may be an end of the suction tube (14) leading from the wound or a short section of tube that terminates with a connector fitting (44) for mating with a matching connector fitting (46) on the end of the suction tube (14).

Airflow and any blood or other fluid aspirated from the wound passes through the fitting (40) in the lid and into the canister (36). The liquid is retained in the canister (36), while the air rises and is drawn through a hydrophobic membrane (50) sealed to the inside of the lid (38). The upstream side of the membrane (50) interfaces with the interior of the canister (36) and the downstream side of the membrane (50) interfaces with an outlet air channel (52). The membrane (50) acts as a bacteria filter. Because the membrane (50) is hydrophobic, it can be used as a shut off mechanism to prevent the canister (36) from overflowing and to prevent contamination from flowing out of the collector (16) toward the suction source. If the canister (36) is allowed to fill high enough for the contents to contact the membrane (50), the membrane (50) occludes and blocks airflow from passing through the collector (16). Blockage of the membrane (50) prevents suctioning more waste from the wound, and as described hereafter, the blockage of reference airflow is detected as an indication of an abnormal operating condition. In other embodiments described hereafter, the level of waste product in the canister (36) can be detected by a capacitance sensor or other detector on the pump unit (102), and the detection used to prevent overfill of the canister (36).

The lid (38) defines the outlet air channel (52) extending from the downstream side of the membrane (50) to a connector (54) for connecting the collector (16) to the portable pump unit (102) or to a tube (58) running to a stationary wall suction system. However, the connector (54) is preferably a proprietary (non-standard) connector that will not connect directly to the standard appliance fitting of a stationary suction system, in order to prevent the collector (16) from being mistakenly connected directly to the suction system without the flow monitoring device (18) and pressure release features described hereafter; connecting the collector (16) directly to a suction system could risk applying too great a suction to the wound. The mating receptacle in the portable pump configuration described hereafter is configured to receive the proprietary connector. The connector (54) includes a sealing element such as an o-ring seal. This arrangement provides that a fresh o-ring is preferably used with each disposable collector (16), as contrasted with other pump connectors where the sealing element is in the pump and will ultimately wear out and cause the system to fail because of leakage.

Preferably the liquid waste sucked from the wound is turned into a gel for ease of disposal and to prevent spilling or splashing. Although the gelling agent could be provided in porous bags, it is preferred to use disks (56) of laminated fiber sheets containing a gelling agent, such as provided by Gelok International. The disks (56) are cut to fit inside of the canister (36) and are stacked on top of each other. The stacked disks (56) cause the liquid to turn to a level surface gel in the canister (36).

Controlled Reference Airflow

Some prior art negative pressure wound therapy systems do not monitor the flow of fluid (air and effluents) being suctioned from the wound dressing (12), while others do so less than optimally by trying to directly sense pressures at the wound. In contrast, the system described herein uses a reference airflow, as may be provided by a calibrated orifice, valve, or filter or by the controlled leak air vent (32, 34), to indicate whether the system is in normal or abnormal operation. The porous plug (34) is calibrated to provide a known reference airflow or controlled leak. A flow rate at or near the reference airflow indicates normal operation, while a flow rate that deviates appreciably (either higher or lower) from the reference airflow indicates abnormal operation. A flow rate higher than the reference airflow indicates leakage, while a flow rate lower than the reference airflow indicates blockage or occlusion or a full waste collector (16).

The reference airflow rate from the calibrated vent (32, 34) is used for monitoring fluid flow and thus for assessing overall system operation. The controlled leak rate should be low to maintain a proper suction at the wound site and a moist healing environment. Preferably the reference airflow is in the range of 50-300 cubic centimeters per minute (cc/min). More preferably, the reference airflow is approximately 100 cc/min. A flow of 50-300 cc/min is low enough to minimize drying and does not significantly alter the suction applied at the wound. Additionally, the flow is low enough to minimize the use of battery power where a portable pump is used as the suction source. A flow of this magnitude is readily obtained by providing a vent hole (32) in the suction tube that is sealed sterile with a porous plug (34). A suitable seal material for the porous plug (34) is a porous plastic manufactured by Porex from sintered high density polyethylene. Such porous materials are routinely employed to admit air into medical fluid lines at a sufficient flow rate to maintain an efficient sterile filtration barrier against microbes.

An advantage of providing the reference airflow is that the tube (14) between the wound packing (12) and the waste collector (16) remains relatively clear of fluids since the continuous flow will encourage rapid movement of a plug of fluid from the wound packing (13) to the collector (16). Liquid aspirated from a wound may contain sufficient blood materials that it could be prone to clotting in a collection tube, lumen, or conduit if allowed to sit in a stationary condition for a period of time, and a clot in a collection line would result in loss of suction being applied to the wound. The reference airflow eliminates this potential problem. Typically, it is expected that the tube (14) could be cleared by the reference airflow in less than ten seconds, depending on the distance.

The range of flows suitable for a reference airflow rate are bounded at the lower end by the permeability of the wound cover (22) and at the upper end by the suction capacity of the suction source or pump. When the wound cover (22) is a semi-permeable material, there will be a natural low level background airflow from air molecules passing through the wound cover (22). This permeation airflow could serve as the reference airflow if the flow monitoring instrument were very sensitive. However, the permeation flow is usually too low and too erratic to be a good reference. Variations in the area of the cover and the possibility of the cover being obstructed by drapes and fluid from the wound can cause the permeation flow to be erratic. Thus, a calibrated vent, such as the porous vent (32, 34) is a preferred reference because it provides a larger and more stable flow rate that masks variations in the permeation flow. For example, Tegaderm® bandage will allow a diffusion of water on the order of 800 grams per square meter per day, which correlates to a flow rate of about 0.5 cc/min over a square meter. Typical wound cover area would be less than a tenth of a square meter, so in approximate terms, the semi-permeable material contributes 0.05 cc/min, or less than 0.1% of a reference airflow of 50 cc/min. Thus, any variation in the background permeation flow is masked by the larger reference airflow.

Flow Monitoring Device for Use with Stationary Suction Source

Figure 4:
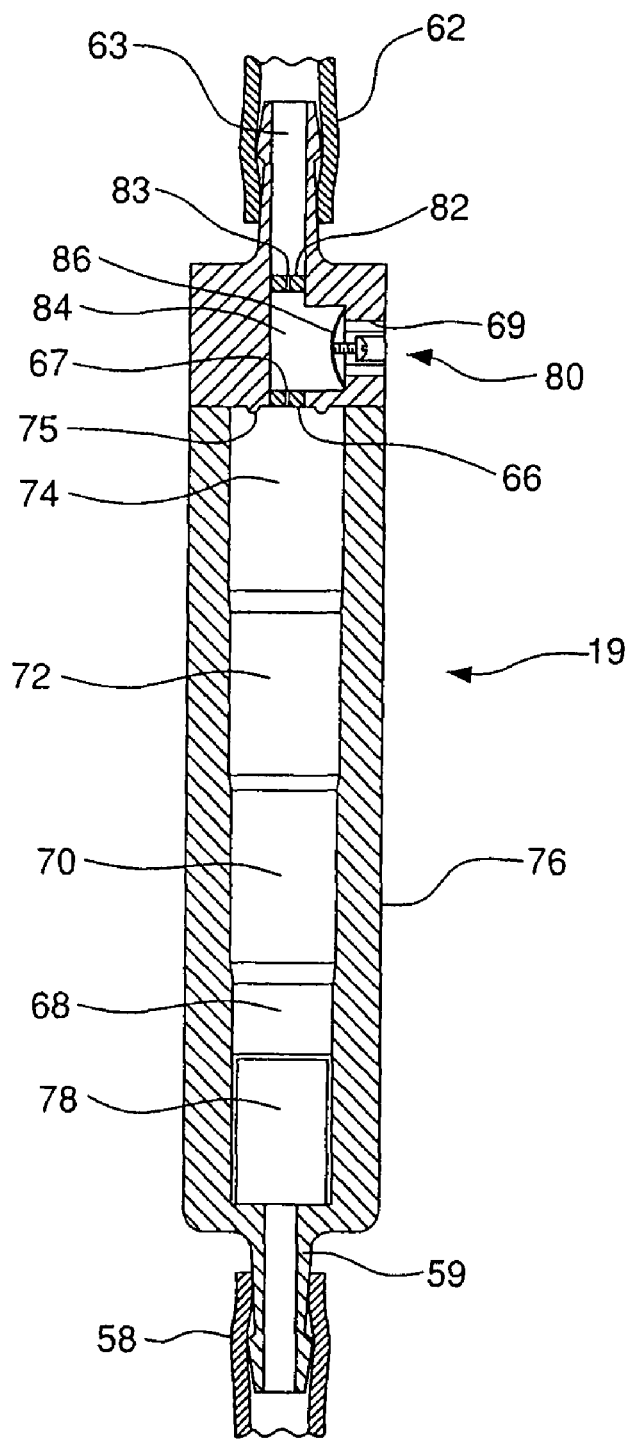
FIG. 4 is a cross-sectional view of a flow monitor of FIG. 1, taken through section 4-4.
Figure 5B:
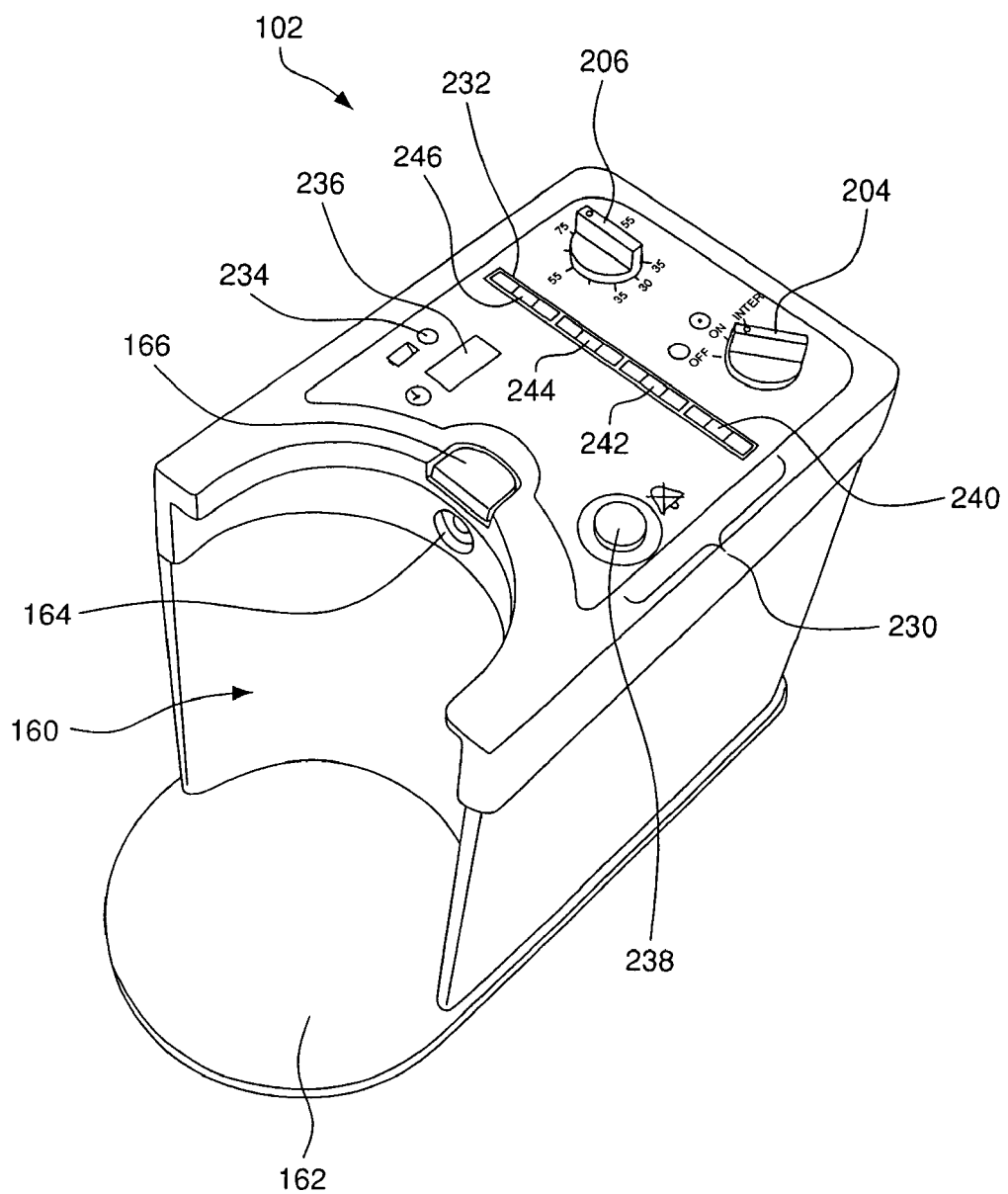
FIG. 5B is a prospective view of the top front of a portable pump unit that may be used in the system of FIG. 5A.

At least two embodiments of the flow monitoring device (18) may be used: a gradated mechanical indicating float meter (19) as shown in detail in FIG. 4 and an electronic non-numerical indicator (232) as shown in detail in FIG. 5B. The float meter (19) would preferably be used in conjunction with a stationary suction source (20) while the non-numerical indicator (232) would preferably be used with a portable pump unit (102) having a flow monitor (206). Other types of flow monitoring and indicating devices, such as target meters or hot wire anemometers could also be used.

In the system (10) of FIG. 1, the flow monitoring device (18) comprises a float flow meter (19) that includes a suction conduit (58) interconnecting between the waste collector (16) and the stationary suction source. One end of the conduit (58) includes a mating connector (60) adapted to receive a proprietary connector (54) on the collector (16). The flow monitoring device (18) is preferably located at the opposed end of the conduit (58) from the collector (16) and attaches directly to an appliance connection fitting (64) associated with the adjustable suction regulator (20) as commonly found on stationary suction systems.

The flow meter (19) provides a visual indication of the flow rate through the system (10). During normal operation, once the flow rate has stabilized following an initial application of suction, the flow meter (19) provides a visual indication corresponding to the reference airflow rate. As long as the flow meter (19) maintains a visual indication of reference airflow rate, the system (10) is operating normally and is free of leaks or blockage, and hence the wound dressing (12) is subject to an acceptable level of suction. When the flow meter (19) provides a visual indication of a deviation to a higher air flow, the system (10) is operating abnormally because a higher air flow indicates leakage. The flow meter (19) may include one or more gradations of flow rates higher than reference airflow to indicate the magnitude of a leak. When the flow meter (19) provides a visual indication of a deviation to a lower air flow, the system (10) is operating abnormally because a lower air flow indicates occlusion or blockage in the system between the wound dressing (12) and the flow meter (19).

FIG. 4 shows a cross-sectional view of the float meter (19). A standard connector (63) on the top end of the indicator attaches to a short conduit (62) connectable to the appliance fitting (64) of the adjustable suction regulator (20). At the bottom end of the flow indicator a standard connector (59) is attached to the suction conduit (58).

As shown in FIG. 4, the flow meter (19) includes a clear tube (76) gradated into progressive sections (68, 70, 72, 74), each section having a different inside diameter. The narrowest section (68) is disposed at the bottom of the flow meter (19) and each successive section (70, 72, 74) moving upwards through the tube (76) is progressively larger in diameter. The gradated markings (not shown) indicate an airflow rate corresponding to various vertical locations along the tube (76). A float (78) is disposed within the tube (76) and serves as an indicator of flow rate through the flow meter (19) and thus through the system (10). Each section (68, 70, 72, 74) indicates a range of flow rates at which the float (78) will reside in that respective section.

The mass of the float (78) works in cooperation with the density (i.e., the pressure) of the flowing fluid and the clearance between the outside of the float (78) and the inside wall of the tube (76). It is typical to use suction in the range of 25-200 mm Hg in wound therapy. Accordingly, the flow monitoring device (18) incorporates a first flow restrictor (66) having an orifice (67) that is calibrated to restrict suction airflow to be less than 20 liters per minute when a controlled level of suction of 100 mm Hg is applied by the suction regulator (20). The density of the float (78) and the inside dimensions of the tube (76) are preferably calibrated for flow at a pressure of 100 mm Hg, although the indicated flow rates at different pressures are readily calculated. Additionally, the response of the float (78) to various flow rates and pressures through the same tube (76) can be changed by changing the density of the float (78).

The float (78) responds to airflow rate and will rise to a level where the dynamic forces are in equilibrium, balancing the upward force of the flow against the downward force of gravity. The gradated tube (76) is in contrast to typical flow indicators for other applications which have tubes with continuously increasing inner diameters. In those types of meters, slight changes in flow rate cause the float to chatter up and down around a height indicative of the flow rate. The use of discrete sections of uniform diameters, but increasing in progression, as the four sections (68, 70, 72, 74) in the tube (76) of the preferred flow indicator (19), reduces the chatter and causes the float (78) to move upward in stages. These stages are selected for discrete flows that provide easily interpreted reference information regarding the suction applied to the wound.

When there is no air flow, or an air flow rate less than the reference airflow, the float (78) rests at the bottom of the tube (76) in the lowest section (68). The lowest section (68) is preferably color-coded blue to indicate a blockage condition, such as a full collector (16) or an occlusion in the fluid path such as a blocked vacuum tube (14). When the flow into the flow meter (19) corresponds to the reference airflow, preferably between about 50 cc/min to about 300 cc/min, the clearance between the float (78) and the bottom section (68) of the tube (76) is such that the flow around the float (78) will cause the float (78) to rise into the next progressively wider section (70). Thus, normal reference airflow will cause the float (78) to rise a discernable amount into the next section (70). The section (70) of normal operation is color-coded green, indicating an acceptable condition.

When flow through the system (10) increases beyond an acceptable level due to a leak in the wound dressing (12), the clearance around the float in the normal position (70) may no longer be adequate to allow the float (70) to remain in this position, and the increased flow will lift the float (78) to a higher section in the tube (76) where the internal diameter is stepped up. The gradated labeling on the outside of the tube (76) provides a visual indication of the extent of the leak condition. The tube (76) includes at least one section (72) of increased diameter to indicate a leak condition and preferably includes two sections (72, 74) to indicate two levels of leak conditions, wherein the lower level leak condition section (72) is disposed immediately above the normal operation section (70), the section (72) having a larger diameter than the section (70), and the higher level leak condition section (74) is disposed immediately above the lower level leak condition section (72), the section (74) having a larger diameter than the section (72). The lower level leak condition section (72) is color-coded yellow, indicating a minor leak requiring repair. The higher level leak condition section (74) is color-coded red, indicating a major leak requiring immediate repair. The stepped up diameters require a significant change in flow before the float (78) will jump from one position to a higher one, thus eliminating the jumpiness that would be encountered with a continuous taper inner diameter as common in flow meters for other applications. Further, the stepped diameter sections (68, 70, 72, 74) reduce user interpretation, thus enhancing ease of use and safety. Additional stepped up diameter sections may be provided to indicate higher leak conditions or finer gradations in the level of leak.

The flow monitoring device (18) also incorporates a safety valve (80) that limits the maximum suction that may be applied through the system (10), guarding against the accidental application of excessively high levels of suction to the wound. It is typical to use suction in the range of 25-200 mm Hg for wound drainage and therapy. Accordingly, the suction limiting feature may preferably be set to limit the suction to no more than approximately 200 mm Hg. The safety valve (80) includes a suction pressure relief chamber (84) formed between the first flow restrictor (66) and a second flow restrictor (82) having an orifice (83). The orifice (83) is preferably about the same size as the orifice (67) in the first flow restrictor (66) to prevent the flow capability of the suction regulator (20) or the pump (103) from overpowering the relief capability of the safety valve (80). A resilient valve mechanism (86) in the relief chamber (84) serves as a release against the application of high levels of suction. The valve mechanism (86) is spring loaded to a predetermined suction setting, such as 200 mm Hg. If the suction pressure in the relief chamber (84) exceeds the predetermined setting, the valve mechanism (86) will open and allow vent air to be drawn into the system (10) from a relief port (69) to prevent excess suction from being applied to the patient's wound.

Protrusions (75) may be provided on the top underside of the interior of the float meter (19) adjacent to the first flow restriction orifice (67) to prevent the float (78) from completely blocking the orifice entry (67) to the pressure relief chamber (84), thus allowing the continued flow of fluid through the system (10) even if a major leak occurs. This allows continued communication of some suction to the wound even at high airflow rates. Alternatively, the protrusions could be located on the top surface of the float (78).

While the flow monitoring device (18) using a float meter (19) has been described in the context of a hospital wall suction system, it can also be used with suction pumps such as the portable pump unit (102), as is described below.

Dehumidifier

Figure 9:
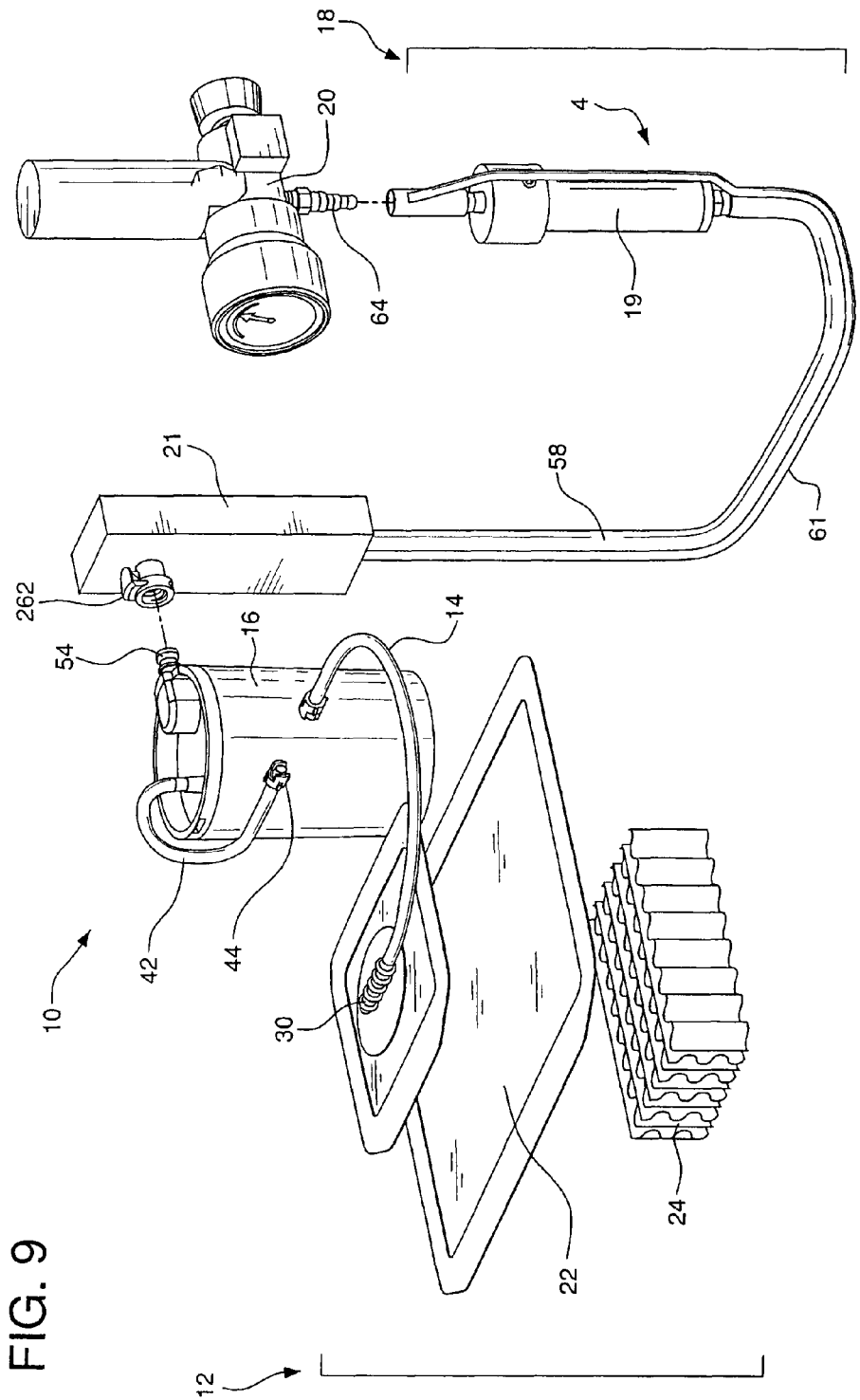
FIG. 9 is an exploded perspective view of an embodiment of a system for negative pressure wound therapy including a dehumidifier.

The negative pressure wound therapy system may include an air filter/dryer or dehumidifier (21) to protect the downstream components, and in particular the suction source, from potential contamination in the form of particulate matter, aerosols, and humidity. The dehumidifier (21) is preferably disposed in a system conduit between the waste collector (16) and the flow meter (19). FIG. 9 illustrates an embodiment of the negative pressure wound therapy system including the air dryer or dehumidifier (21) conveniently integrated into a mount for the waste collector (16).

The dehumidifier (21) may include a particle filter (68) for removing airborne dust as may be encountered when the flow meter (19) is disconnected from the collector (16) for periodic changeover. Humid air exits the waste collector (16) after any liquids have been substantially removed from the wound exudates, but sufficient moisture may remain in the air such that the relative humidity is at or near 100%. At such a high relative humidity, any drop in temperature or pressure may cause condensate to drop out of the air. Accordingly, the dehumidifier (21) removes moisture from the humid air that could otherwise effect the calibration of the flow meter (19). A desiccant or other means of humidity control can be placed in the dehumidifier (21), as required.

Figure 10:
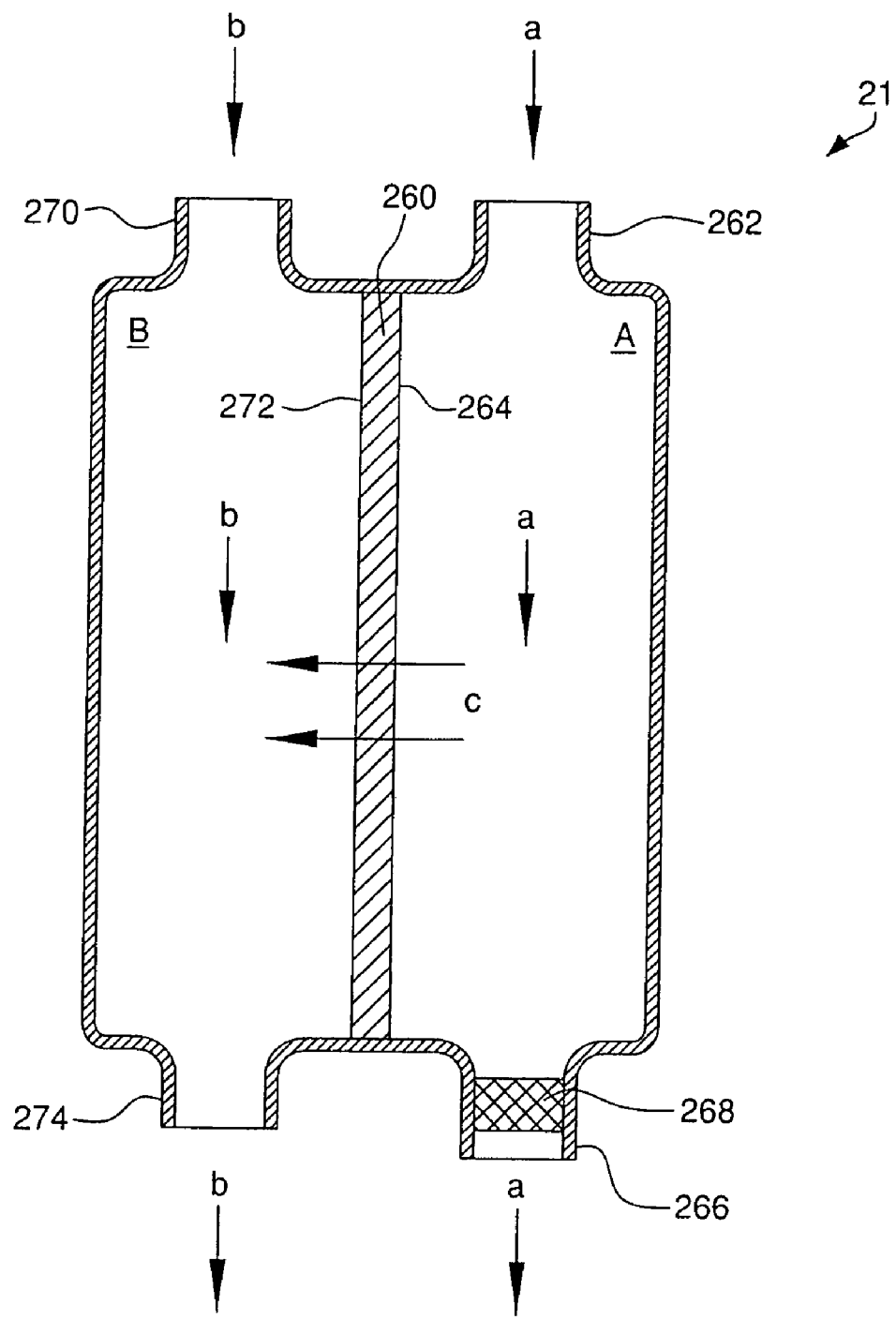
FIG. 10 is a schematic cross-sectional view of the dehumidifier of the system of FIG. 9.

The dehumidifier (21) may also operate by removing moisture from the humid air exiting the waste collector (16) by causing the humid air to pass across one side of a membrane (260) that is impermeable to air but is permeable to water vapor, and concomitantly causing ambient room air, at a relative humidity level much less than 100%, to pass across an opposite side of the membrane (260). FIG. 10 schematically illustrates operation of the dehumidifier (21). Due to the properties of the air-impermeable, water vapor-permeable membrane (260), moisture from the higher humidity system air is transferred to the lower humidity room air. The lowered humidity of the system air exiting the dehumidifier (21), at a relative humidity below 100%, prevents the formation of condensation droplets in downstream components such as the flow meter (19) or the suction source.

The dryer or dehumidifier (21) includes two separate airflow paths (A) and (B) separated by the generally air-impermeable, water vapor-permeable membrane (260). Because the flow meter (19) is a precise device that indicates the quantity of system fluid flow, the dehumidifier is constructed so that the membrane (260) is air tight and air-impermeable such that air from the room side (B) cannot mix with air on the system side (A). At the same time, the membrane (260) should have good water transport properties to remove water from the system air. The membrane (260) is ideally a Dupont Nafion membrane with known water vapor transport properties, although other similar or equivalent membrane materials may be used. System air (a), having high humidity, flows from the waste collector (16) into a dehumidifier inlet (262). System air (a) flows across a surface (264) of the membrane (260) and then out a dehumidifier outlet (266) after passing through a particulate filter (268). System air then flows to the flow meter (19). Ambient air (b) enters the a dehumidifier inlet (270) and flows across a surface (272) of the membrane (260). Ambient air (b) exits a dehumidifier outlet (274) and is drawn into the suction source via a conduit (61).

System air (a) exiting the waste collector (16) is generally very humid (up to 100% relative humidity) due to the liquids that are being collected from the wound. Ambient air (b) is generally less humid; most hospital environments may have relative humidity in the 50% range, depending of course upon the prevailing outside temperature and weather conditions. The resultant moisture gradient across the membrane (260) causes water vapor (c) to be transported through the membrane (260) from the system air flowpath (A) to the ambient air flowpath (B), thus removing water vapor from the system air. As a result, the relative humidity of the system air is reduced to less than 100%, preventing condensation droplets from forming in the flow meter (19) and minimizing the chance that the flow meter (19) will malfunction due to water droplet formation.

Figures 11A, 11B, 11C:
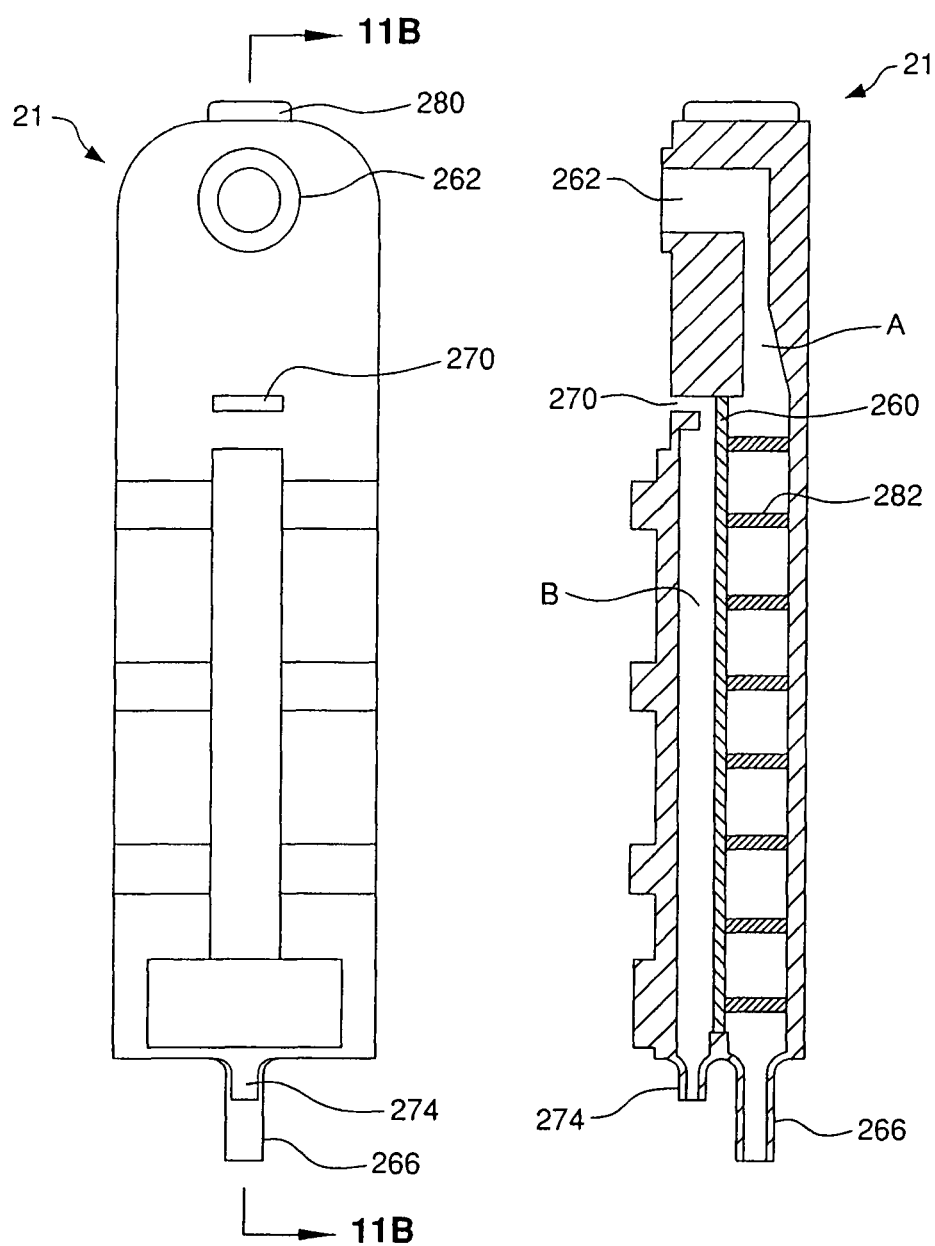
FIG. 11A is a front view of the dehumidifier.
FIG. 11B is a cross-sectional view of the dehumidifier of FIG. 11A taken through section 11B-11B.
FIG. 11C is a top view of the dehumidifier of FIG. 11A.

FIGS. 11A, 11B, and 11C illustrate the dehumidifier (21) in more detail. In a preferred embodiment, as shown, the dehumidifier (21) also serves as a mount for the waste collector (16). The system air inlet (262) serves to accept the outlet connection fitting (54) of the collector (16), which may be secured to the dehumidifier (21) by a spring-loaded latch (280). A set of extending nubs (282) support the membrane (260) inside the dehumidifier (21) and provide flow channels for the system air to pass on the (A) side and position the membrane (260) to provide a flow passage for ambient air to pass on the (B) side.

Portable Pump Unit for Use as the Suction Source

The system (10) described herein may be used in conjunction with a stationary suction source as provided in most medical buildings, or may be used in conjunction with electrical power pumps to provide suction for wound therapy. However stationary suction sources, and even electric power pumps that may be moved from outlet to outlet, have limited portability. Accordingly, an embodiment of the system (100) provides a truly portable battery powered pump unit (102). In a portable pump embodiment (100) of the suction system, as shown in FIG. 5A, the suction source is a portable suction pump unit (102) instead of a stationary suction source. Additionally, the use of an electronically controlled suction pump, for example by using a pump unit controller (200) as illustrated in FIG. 6, provides the ability to incorporate further advanced control, monitoring, and alerting features into the negative pressure wound treatment system (100).

The pump unit (102) connects to the same patient circuit, including the wound dressing (12) and the waste collector (16), as described in regard to the negative pressure wound therapy system (10). The pump unit (102) preferably operates on low voltage DC power and has an onboard power source (222) such as a 12 volt battery. The pump unit (102) may also be adapted to be powered through a power cord from a standard AC power socket using a suitable AC/DC power converter (220), which may be combined with a battery charger to recharge the battery (222) during use. The pump unit (102) can receive DC power either from the converter (220), when plugged in, or from the battery (222), when used un-plugged.

The pump unit (102) is configured to produce controlled levels negative pressure. As shown in detail in FIG. 5B and schematically in FIG. 6, the pump unit (102) has a Mode Selector switch (204) to select between On, Off, and Intermittent control modes, and a pressure selector dial (206). A prescribed pressure setting is selected using the pressure selector dial (206). The available range of setpoints is preferably between about 30 mm Hg and 100 mm Hg, and is more preferably between about 30 mm Hg and 75 mm Hg. In one embodiment, discrete pressure setpoints of 20, 30, 40, 50, 60, 70, and 75 mm Hg are offered. Additionally, setpoint choices of 100, 125, 150, 175, and 200 mm Hg may be offered. The pump power may be placed into a On state, an Off state, or an Intermittent state using the Mode Selector switch (204). In the Off state, the pump unit (102) will not operate. In the On state, the pump unit (102) will operate based on the selected pressure setpoint. In the Intermittent state, the pump unit (102) will operate cyclically between a higher pressure setpoint selected by the selector dial (206) and a prescribed lower pressure setpoint, as will described in greater detail below.

Figure 6:
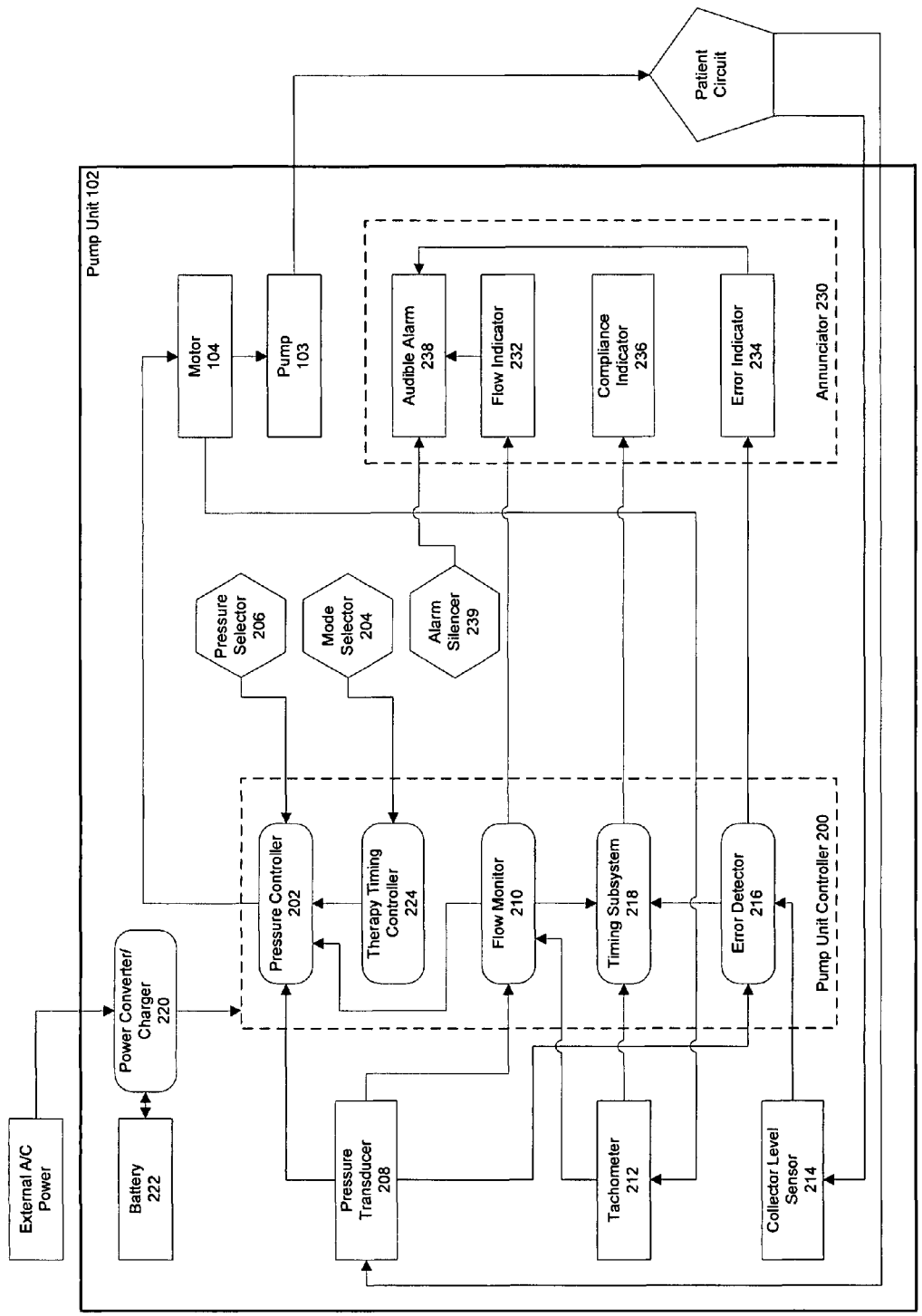
FIG. 6 is a control schematic diagram corresponding to an embodiment of a pump unit.

Referring to the schematic diagram of FIG. 6, the portable pump unit (102) preferably includes a positive displacement air pump (103), a variable speed DC motor (104), a tachometer (212), a pressure transducer (208), a level sensor (214), a pump unit controller (200), and an annunciator (230). The pump unit controller (200) comprises a pressure controller (202), a flow monitor (210), an error detector (216), a therapy timing controller (224), and a timing subsystem (218). The annunciator (230) comprises a flow status indicator (232), an error indicator (234), a compliance indicator (236), and an audible alarm (238). The flow status indicator (232) is capable of indicating normal or abnormal flow conditions, and the error indicator (234) is capable of indicating other status, fault, or alarm conditions. In the depicted embodiment, the pump unit controller (200) may include one or more of a microprocessor, solid state electronic device, electromechanical devices, mechanical or pneumatic devices, or other equivalent control elements. If a microprocessor is used for performing functions including pressure control, flow monitoring, error detection, and status and alarm annunciation, a suitable processor is a Microchip 16 Series, part number 16F688, it being understood that other similar programmable logic devices could be used.

Vacuum Pressure Control

Referring to the embodiment schematically illustrated FIG. 6, the pump unit controller (200) includes a vacuum or suction pressure controller (202) for maintaining a negative pressure in the wound. The pressure controller (202) is independent of the flow monitor (210), regardless whether the pressure controller (202) and/or flow monitor (210) use a microprocessor or an alternative means such as solid state control circuit. The pressure controller (202) regulates operation of the pump unit (102) based on a signal from a pressure transducer (208) that monitors the negative pressure produced at the suction side of pump (103). The pressure transducer (208) is preferably located in a conduit between the waste collector (16) and the pump (103). Alternatively, a low-cost pressure transducer (208) may be placed directly within the wound cavity and the signal from the transducer (208) conducted via wires to the pressure controller (202).

The pressure controller (202) receives a setpoint from the user positionable pressure selector dial (206). In an embodiment, the pressure controller (202) includes a solid state logic device and the selector dial (206) changes the resistance of a variable resistor to produce an electrical signal representing the selected pressure setpoint. The pressure controller (202) receives the selected pressure setting as an input, and sets an upper limit and a lower limit in a range above and below the selected pressure setpoint. The range between upper limit and the lower limit is selected to provide a reasonably stable suction level while minimizing the on-off cycling of the pump motor (104). A range of approximately 10 mm Hg is preferred to optimize patient comfort and to minimize noise. The pressure controller (202) will function to maintain the pressure sensed by the transducer (208) between the two limits defining the range about the pressure setpoint. Such control circuits are commonly employed in industrial applications as well as in hospital central suction systems.

When the pump unit (102) is initially turned On by the Mode Selector switch (204), the pressure controller (202) causes the pump motor (104) to start running, driving the positive displacement pump (103). The pump motor (104) continues to run until the pressure transducer (208) detects pressure at or exceeding the upper vacuum limit of the pressure range set by the pressure controller (202) in response to the pressure setpoint on the selector dial (206). The pressure controller (202) continually compares the pressure signal from the pressure transducer (208) to the setpoint limits bounding the range about the operator-selected pressure setpoint. Once the upper control limit is reached, the pressure controller (202) turns off the pump (103). Normal reference airflow in the system (10) will cause pressure at the transducer (208) to decay towards the lower limit of the control range. Once the detected pressure has reached the lower control limit, the pressure controller (202) will turn the pump (103) back on, and the process is repeated cyclically. Thus, the pressure transducer (208) senses the current negative pressure in the system (10) and the pressure controller (202) turns the pump (103) on and off accordingly to maintain negative pressures that are within the selected desired range.

The motor (104) is preferably a variable speed DC brushless motor. However other styles of DC motors are acceptable, as well as AC motors that can be equipped with variable outputs. When a variable speed motor is used, the speed is controlled via a pulse width modulation (PWM) feature of the pressure controller (202). Variable speed control allows for efficient use of DC power. When a constant speed motor is employed, the on/off time is varied such that the motor is cycled on and off at the most efficient operating speed.

The positive displacement pump (103) preferably uses a diaphragm style pump with inlet and outlet check valves. The diaphragm pump crankshaft is operationally connected to the shaft of the variable speed motor (104). Other positive displacement pumps may be used, such as peristaltic, piston, lobe, syringe or rocking piston pumps.

The tachometer (212) can be used to indicate the rotational speed of the motor (104) or pump shaft. Within the generic term "tachometer" various forms of motor or pump speed sensors may be used. For example, Hall sensors and encoders are commonly employed on DC brushless motors to indicate motor RPM (revolutions per minute). It is also possible to sense back-EMF in brush versions of DC motors to determine motor shaft rotation speed. In an AC motor driven pump, an oscillating bar with a magnet mounted to an end may be excited by an AC coil, thus driving a diaphragm, and a count of the oscillations delivered by the coil can be used as an indicator of pump speed. Regardless the type of tachometer, such a tachometer can be used to infer or determine the flow rate of fluid displaced by the pump unit (102). Because there is a direct correlation between the speed of the positive displacement pump (103) and the actual volume of fluid displaced at a given operating pressure, a measurement of the pump speed combined with a measurement of pressure at inlet of the pump (103), as measured by the pressure transducer (208), can be used to calculate flow rate. Thus, measuring the speed of the positive displacement pump (103) is a surrogate for direct airflow measurement.

As described above, the pressure controller (202) will cause the pump (103) to run as necessary to maintain the level of vacuum pressure sensed by the transducer (208) within the desired range of the selected negative pressure setpoint. The pressure controller (202) may modulate the on-time duration of the pump (103) to maintain the negative pressure in the desired range. The on-time duration of the pump (103) can be increased or decreased as required by the pump controller (202) to achieve greater or lesser suction, respectively. When a variable speed motor (104) is used, the motor speed can also be adjusted by pulse width modulation, separately from or in combination with the on-time duration, to operate the motor (104) at an efficient speed. Accordingly, the pressure controller (202) can adjust either or both the on-time duration and pump speed to maintain the negative pressure in the range established by the selected pressure setpoint. Thus, the pressure controller (202) operates based on sensed pressure, and not on sensed air flow. This allows the pressure controller (202) to function independently from the mechanisms for detecting, monitoring, and displaying the status of flow in the system (10) that are embodied in the flow monitor (210) and the error detector (216).

Flow Monitor and Flow Status Indicator

As shown in FIG. 6, the flow monitor (210) can be adapted to monitor pump activity (i.e., on-time duration and speed) as an indicator of the flow rate of air through the negative pressure wound therapy system (10). The flow monitor (210) is coupled with the flow status indicator (232) in the annunciator (230) to provide audible and visual indication of the status of operation of the system (10) by comparing the fluid flow rate to the reference airflow rate and annunciating indicators of normal or abnormal operation. The flow monitor (210) functions independently from the pressure controller (202). Preferably the flow monitor (210) receives input from sensors that detect pump motor activity, determines a flow rate based upon the motor activity sensor inputs, identifies deviations from the reference airflow rate, and provides a signal to the flow status indicator (232) identifying either a normal state of operation or one of at least two abnormal states of operation.

The flow monitor (210) is capable of performing flow monitoring functions necessary to compare the fluid flow rate to the reference airflow rate and determine normal or abnormal operational status. To monitor flow rate, revolutions of the motor (104) or positive displacement pump (103) are counted over a period of time, and the count, along with the pressure transducer (208) measurement, is provided as input to the flow monitor (210). An algorithm in the flow monitor (210) correlates the rate of motor revolutions (i.e., count per time), adjusted for pressure, to determine the volumetric flow rate of air passing through the pump (103). The flow monitor (210) compares the calculated flow rate to the known reference airflow rate to determine fault conditions.

The flow rate detected by the flow monitor (210) is converted into a signal that illuminates a display bar on the flow status indicator (232). A flow rate that is less than the reference airflow rate is displayed as abnormal operation on the flow status indicator (232), indicating an occlusion in the negative pressure system (10). Most commonly, a low flow rate condition is caused by a full waste collector (16), but other causes may include a pinched or blocked tube (14) or blockage of the controlled vent (32, 34). A user can distinguish between a full collector (16) condition and a blocked tube (14) condition by viewing the flow status indicator (232) in combination with the error indicator (234) to determine if the level sensor (214) has indicated a full collector (16), as will be discussed below. A flow rate that is comparable to the reference airflow rate is displayed as normal operation on the flow status indicator (232), indicating an acceptable flow rate. For purposes of determining normal operation, a range is established about the reference airflow rate, such that a flow within that range is deemed normal and a deviation upward or downward outside that range is deemed abnormal. A flow rate that is higher than the reference airflow rate is displayed as abnormal operation on the flow status indicator (232), indicating a leak in the negative pressure system (10). Preferably, two levels of leak condition are indicated, a low level leak and a high level leak, to provide a gradated alert to the caregiver indicating the urgency with which the seal of the wound cover (22) must be addressed.

Referring particularly to FIG. 5B, a preferred flow status indicator (232) for use in conjunction with the flow monitor (210) comprises a color-coded bar display having four differently colored regions to indicate four different status conditions. In particular, the bar display preferably includes regions to indicate low flow, normal reference airflow, low-level leak, and high-level leak. In the depicted embodiment, the bar display includes a region of blue LEDs (240) to indicate a flow rate lower than the reference airflow rate range, a region of green LEDs (242) to indicate a flow rate within the reference airflow rate range, a region of yellow LEDs (244) to indicate a flow rate at a low level above the reference airflow rate range, and a region of red LEDs (246) to indicate a flow rate at a high level above the reference airflow rate range. It is readily apparent that a wide variety of non-numerical indicators may be used to display three, four, or more status conditions, including but not limited to an arrow translating up and down a linear scale with demarcated regions, an arrow rotating around a circular scale with demarcated regions, a series of lights such that the number of illuminated lights indicates the status condition, one or more blinking lights such that the frequency of blinking indicates the status condition, and illuminated symbols representative of said flow ranges. Additionally, an audible indicator or alarm (238) may be used to indicate an abnormal operating condition, separately from or in combination with a visual indicator. For example, a beeping or continuous tone may be used to indicate abnormal operation, with a different tone pitch, tone duration, or beeping frequency used to indicate each different abnormal condition, while a normal condition would be indicated by the absence of an alarm tone. An alarm silencer or alarm acknowledge button (239) is provided to silence the audible alarm (238) until the abnormal condition has been corrected.

The gradation of ranges of the flow status indicator (232) may be linear or non-linear and may be adjusted depending on the particular conditions in which the negative pressure wound treatment system is applied. In one embodiment, the reference airflow rate range is preferably defined as a ±10% band about the reference airflow rate, a low flow rate is defined as less than 90% of the reference airflow rate, a low-level leak flow rate is preferably defined as between 110% and 125% of the reference airflow rate, and a high-level leak flow rate is preferably defined as greater than 125% of the reference airflow rate. In another embodiment, where tighter flow rate control is desirable and possible, the reference airflow rate range is defined as a ±5% band about the reference airflow rate, a low flow rate is defined as less than 95% of the reference airflow rate, a low-level leak flow rate is defined as between 105% and 115% of the reference airflow rate, and a high-level leak flow rate is defined as greater than 115% of the reference airflow rate. Tighter flow control may be required, for example, where the wound being treated is smaller such that a low-level leak would be more likely to compromise the vacuum being applied to the wound dressing (12). In yet another embodiment, where less tight flow rate control is desirable and possible, the reference airflow rate range is defined as a ±15% band about the reference airflow rate, a low flow rate is defined as less than 85% of the reference airflow rate, a low-level leak flow rate is defined as between 115% and 130% of the reference airflow rate, and a high-level leak flow rate is defined as greater than 130% of the reference airflow rate. Less tight flow control may be desired, for example, where the wound being treated is larger such that a low-level leak would be less likely to compromise the vacuum being applied to the wound dressing (12). It is readily appreciated that each of the status condition ranges may be adjusted independently to optimize the characteristics of the flow status indicator (232) for a particular application.

In the embodiment shown in FIG. 6, when the pump (103) is independently turned on and off by the pressure controller (202) to maintain setpoint pressure, the pressure sensed by the transducer (208) will oscillate between the upper control limit and the lower control limit. The period of this oscillation is related to the reference airflow rate, the normal rate of permeation through the wound cover (22), and any leakage in the wound dressing (12). Because the reference airflow rate and the normal rate of permeation through the wound cover (22) should be relatively constant, the higher the leakage in the wound dressing (12), the shorter the period of oscillation will be. Thus, the time intervals between the pump turning on or off can be detected by the flow monitor (210) and used as a rough measure of fluid flow rate through the system.

Where the pump motor speed is also controlled via a pulse width modulation (PWM) control to make the use of DC power more efficient, the flow monitor (210) can also correlate the on/off intervals with pulse rate to determine flow rate. In normal operation, the positive displacement pump (103) will output a given number of pulses for each revolution of the pump. The pulse signals can be supplied as an input to the flow monitor (210). These pulse signals can be used to determine the number of pumping strokes the pump (103) has performed over a period of time, and combined with the known volume of each pump stroke, can provide very close approximation of the pumped volume per time (i.e., volumetric flow rate). The flow monitor (210) continually counts the pulses being output from the pump (103), combined with the pressure measured by the transducer (208), to calculate the volume of air flow. When taken in combination with a time measurement, pump pulses per unit time represent the airflow rate. In a presently preferred embodiment, the time measurement is based on the off cycles of the pump motor: from the time the pump (103) turns off, until the next time the pump turns off, the flow monitor (210) counts the pulses and divides by the time between each motor off condition to determine the flow rate through the negative pressure system (10).

As discussed previously, abnormal conditions in the suction therapy system are detected as deviations from the expected flow (i.e., the reference airflow rate) through the system. In yet another embodiment, the reference airflow rate range is calibrated to a tolerance within approximately 50-100 cc/min higher or lower than the airflow produced by the calibrated vent (32, 34) on the end of the suction tube (14). A flow rate within this range is denoted as normal operation. If the flow monitor (210) determines that the pump is not running at a normal duration to maintain the setpoint negative pressure, the flow status indicator (232) of the annunciator (230) provides a visual indicator and audible alarm to alert the caregiver. For a PWM controlled pump (103), an increase in the on-time of the motor (104) is proportional to increase of air flow in the system (10). The flow monitor (210) uses an algorithm to correct the air flow rate based on the actual pressure in the system (10). Any leak in the wound dressing (12) will require more flow to maintain the require suction level, such that the leak will be compensated for by an increase in the on-time of the pump (103). When the on-time increases to equate to a flow of approximately 3 liters per minute, the flow status indicator (232) provides a visual indicator to alert the caregiver to inspect and repair the leak in the wound dressing (12). If the caregiver is able to correct the leak, the visual indicator will turn off. If the fault condition is not addressed (by resealing the wound site) within a prescribed timeframe, preferably about one minute, the flow monitor (210) will cause the flow status indicator (232) to activate the audible alarm (238). Nevertheless, even when a leak condition exists, the pump (103) will continue to run as directed by the pressure controller (202), delivering some level of suction until the condition is corrected or the pump unit (102) is turned off.

The flow monitor (210) can also sense the loss or drop of flow below the reference airflow range. A drop in flow may be caused by various fault conditions, including the tubing (14) to the waste collector (16) becoming clogged with wound exudates, the tubing (14) being crimped shut by bending or squeezing, the waste collector (16) becoming full, and the filter (50) becoming occluded. These conditions also result in the loss of negative pressure at the wound. When a reduction in flow below the reference airflow range is sensed, and the flow status indicator (232) activates a visual indicator to alert the caregiver of a blockage condition.

Intermittent Suction Regime

It is sometimes desirable to provide suction in an intermittent fashion to benefit the healing process. Prior processes involve allowing the negative pressure system to vent to atmospheric pressure for a period of time to allow for reperfusion of tissue. However, allowing the system to completely vent to atmosphere results in a complete loss of suction on the wound dressing (12) and the resultant loss of any benefit that suction could play in maintaining an airtight seal around the wound. The present invention solves this problem by varying the suction between two distinct levels: a first higher vacuum level selected by the pressure selector dial (206) and a second reduced vacuum level of 20-25 mm Hg. The selected higher level is used to apply the beneficial therapeutic effects of suction. The second reduced level is below capillary bed pressure, so reperfusion of tissues will occur in this lower setting, while the wound dressing (12) maintains at least some level of suction to help keep the dressing seals in place and to maintain the reference airflow, thus preventing reflux (by ensuring continuous one-way flow) and clotting in the system tubing. With this type of intermittent pump operation, the reference airflow should be selected such that it is maintained even at the reduced level, or else any annunciator (230) outputs associated with low airflow should be disarmed by the flow monitor (210) during reduced suction intervals as well as the ramp-up and ramp-down intervals.

To effect intermittent suction, the pressure controller (202) can cyclically reset the pressure setpoint between the selected pressure and the second reduced pressure. When the Mode Selector switch (204) is set to Intermittent mode, the programming in the therapy timing controller (224) uses a time interval for switching the pressure setpoint provided to the pressure controller (202) back and forth between the selected pressure and the second reduced pressure. In an embodiment, to enter the reduced pressure cycle of the intermittent mode, the therapy timing controller (224) activates a transistor that adds a resistance to the pressure controller circuitry, effectively resetting the pressure setpoint to the second reduced pressure.

Waste Collector Docking Station and Fill Indicator

As illustrated in the embodiment of FIGS. 5A and 5B, the pump unit (102) includes a docking station (160) for supporting the waste collector (16) which collects liquids aspirated from the wound. The waste collector (16) is disposed in the system between the wound dressing (12) and the pump (103). The waste collector (16) preferably comprises a transparent plastic canister (36) having right circular cylinder profile and fill-level markings along the height of the cylinder. The inlet connection (40) of the waste collector (16) is interconnected to the tubing (14) extending from the wound dressing (12), and the outlet fitting (54) of the waste collector (16) has an o-ring seal. The portable pump docking station (160) supports the waste collector (16). The docking station (160) has a concave profile conforming to an external section of the collector (16) and a generally circular base (162) to support the waste collector (16) when docked. The pump unit (102) includes a releasable latch fitting (164) in an upper wall of the docking station (160) that is adapted to receive the connection fitting (54) of the waste collector (16). The fitting (54) is inserted into the latch fitting (164) and latched in place. The waste collector (16) may be released and removed from the docking station (160) by depressing the release button (166) to release the fitting (54) from the latch fitting (164).

The pump unit (102) provides the ability to detect a filled waste collector (16) without the need to measure differential pressures across the membrane (50), as is required in existing systems. Differential pressure measurement can be problematic because partially clogged membranes can lead to erroneous readings and interpretations. In a preferred embodiment, the pump unit (102) employs positive level detection as a direct indication of the fill status of the waste collector (16). In particular, the pump unit (102) may include a level sensor (214) proximate to the docking station (160) for detecting when the level of waste in the collector (16) equals or exceeds a level which indicates a filled collector condition. The level sensor (214) can take many forms, such as capacitance, optical, ultrasonic, contact wire, float, and others similar sensing mechanisms. A preferred level sensor (214) is a capacitance detector such as a Model #BC 10-QF5 sensor manufactured by Turck, Inc. The level sensor (214) can be positioned in the pump unit (102) at a desired level proximate to the docking station (160) and has the ability to read a change in capacitance as caused by the presence of an ionic fluid. A capacitance level sensor is capable of sensing capacitance through surfaces such as the wall of the canister (36), so no elements of the sensor (214) are exposed to the wound exudate. Capacitance type detection is also tolerant to conditions such as mist or fogging.

Direct level detection by the level sensor (214) also allows differentiation between a filled waste collector (16) and an occluded condition such as blockage in the tubing (14) that may result in a deviation from the reference airflow range. Based on a signal provided by the direct level sensor (214) to the error detector (216), the error indicator (234) of the annunciator (230) can illuminate a visual indicator and/or an audible alarm distinct from the flow status indicator (232) used to display normal or abnormal flow conditions. Providing the clinician a distinction between filled waste collector condition and an occlusion makes the system easier to use and less prone to user error.

Since the patients may be mobile or need to be transported, there is a potential that agitation and motion can create artifact where fluid may splash and cause a false positive indication of a filled waste collector (16) and subsequently trigger an unwarranted signal or alarm. An algorithm may be used by the error detector (216) to minimize the likelihood of this false indication. The algorithm incorporates a time delay and a sampling rate. For example, a sampling rate of 10 milliseconds and a delay of 4 seconds has been shown to be an effective set of parameters for reducing false full indications due to the motion artifact. Preferably the algorithm is programmed into the error detector (216) of the pump unit controller (200).

Timing Subsystem and Compliance Monitor

The pump unit controller (200) may have a timing subsystem (218) for recording and accumulating time units corresponding to periods of time when the pump (103) is running. Preferably the timing subsystem (218) records and accumulates the pump operating time units based upon inputs from various sensors. For example, the timing can be started and stopped by signals from the Mode Selector switch (204), or signals that can detect when the pump is running from the tachometer (212) or other sensor. The timing subsystem (218) preferably is capable of providing time reports of the time history of operation of the pump (103). The time reports may include a record of runtime intervals, a record of the date and duration of runtime intervals, a record of total accumulated runtime, a record of accumulated compliant runtime, and a record of runtime remaining on a preset runtime period.

The timing subsystem (218) of the pump unit controller (200) may include an onboard compliance monitor as part of the timing function. A compliance indicator (236) alerts the caregiver to deviations from the normal application of suction to the wound over time and is a useful adjunct to the application of negative pressure wound therapy. The compliance monitor may compute the number of hours that suction has been within ±5 mm Hg of a pressure setpoint. Medical experience has shown that suction is preferably applied for 22 of any 24 continuous hours to be effective. The compliance indicator (236) can show and record in numerous ways the number or percentage of compliant hours of suction therapy for a given therapy period.

The timing subsystem (218) may be connected to alarms which indicate abnormal operating conditions due to leak or occlusion. The timing subsystem (218) may also be used to indicate time remaining until scheduled maintenance or cleaning, or to indicate time used or remaining on a billing plan where the payments for usage are based upon time units either on return or pre-paid in advance. When the pump unit (102) is sold or leased in this manner, e the timing subsystem (218) has the ability to record and accumulate time units corresponding to periods of time when the pump (103) is running and for providing reports of runtime, including compliant runtime when the wound treatment system (10) is operating normally.

Error Detection and Display

The pump unit (102) may include warning or caution lights indicating pump operating parameters, or errors other than those that are detected by deviations from the reference airflow rate. Numerous combinations of visual and audible indicators may be sued to display such status, fault, or error conditions. In the schematic embodiment of FIG. 6, a visual error indicator (234), separate from the flow status indicator (232), provides additional trouble shooting assistance. Various errors may be detected based on sensor signals received by the error detector (216). The error indicator (234) preferably includes an alphanumeric error display, and the error detector (216) can cause the error display to provide indications that correlate to at least following errors: overpressure (i.e., suction exceeding a prescribed limit), missing waste collector, pressure transducer failure, low battery, low operating time remaining, and attachment of incorrect power supply.

Overpressure is the condition where a runaway pump (103) could cause potentially high negative pressures to be delivered to the patient. The error detector (216) continually polls the output of the pressure transducer (208) and compares it to a stored maximum allowable pressure. If the maximum allowable pressure is exceeded for a predetermined time period, then the pressure controller (202) causes the pump (103) to stop operating and an overpressure error is indicated on the error indicator (234).

A missing waste collector condition occurs if the pump (103) is activated without a waste collector (16) installed in the docking station (160) and connected to the latch fitting (164). This condition can occur at startup or during operation, and is detected by the error detector (216) as flow through the system exceeding a certain level without a corresponding minimal increase in pressure. The threshold flow rate for detecting a missing waste collector is typically set to be greater than the increased flow that would be expected from a wound a dressing that was removed or compromised. When so detected, a missing waste collector error is indicated on the error indicator (234).

A pressure transducer failure can take two forms: an excessively high reading indicative of high vacuum or an open circuit (no pressure reading). A high vacuum reading would be interpreted as an overpressure condition, as described above, and would result in a fail-safe deactivation of the pump (103). An open circuit failure appears as zero pressure output, so if the error detector (216) detects air flow but zero pressure, a transducer failure error is indicated on the error indicator (234).

A low battery charge is determined by the error detector (216) polling the battery output voltage when the pump unit (102) is not plugged into an external electrical power source. When a threshold low voltage level is crossed, a low battery error is indicated on the error indicator (234).

Low operating time remaining is associated with the timing feature of the pump unit controller (200) when it is used to indicate time remaining until scheduled maintenance service or time remaining on a pre-paid rental plan. The timing system (218) constantly accumulates runtime and time remaining to a target time, such as the number of pre-paid hours. The error detector (216) can be set to a time remaining threshold, such that when the accumulated time indicates that time remaining has dropped below the threshold, a low time error is indicated on the error indicator (234).

Incorrect power supply detection is to guard against providing excessive voltage to the system. This is accomplished by comparing the input voltage to a set maximum level and detecting if voltage exceeds the maximum level. The error detector (216) detects the excess voltage and shuts down the pump (103), and an incorrect power error is indicated on the error indicator (234).

Collection Line Pulse System

The pump unit (102) may include a collection line pulse feature to ensure that the collection line is maintained as clear as practical to minimize the amount of fluid in the line and ensure accurate delivery of the negative pressure. When the flow monitor (210) begins to detect a deviation from the reference airflow rate so as to indicate an occlusion, the pressure controller (202) can temporarily reset the pressure setpoint temporarily to a pressure higher than the selected pressure, causing the pump (103) to start or to increase in speed. This pump activation or acceleration causes a pressure pulse of transient high negative pressure in the system conduit to clear the tube (14) between the wound dressing (12) and the waste collector (16). The pressure pulse is initiated prior to the illumination of an occlusion indication on the flow status indicator (232). An occlusion indication will not occur if the pressure pulse is followed by decay in the pressure measured by the pressure transducer (208), because a decay in pressure would indicate a cleared collection line and the absence of an occlusion. Once the flow monitor (210) again detects a normal fluid flow rate, the pressure controller (202) resets the pressure setpoint to the selected pressure.

Additional Features

In order to enhance safety of the negative pressure wound therapy system (10), the pressure controller (202) can operate independently of the flow monitor (210) and error detector (216) in the pump unit controller (200). This provides a measure of system redundancy in the event that one or the other function should fail. Should the pressure controller (202) fail, the flow monitor (210) and/or error detector (216) are capable of shutting down the pump unit (102), and should the flow monitor (210) fail, the pressure controller (202) will continue to provide suction to the wound.

The pump unit (102) may have a charcoal filter element (not shown) for controlling odors that may emanate from the patient through the pump (103). This element is placed on the outlet of the pump (103) and can be readily changed and replaced. Also, desiccants can be used in conjunction with the filter to minimize moisture in the exhaust from the pump (103).

Positive displacement pumps typically employ check valves which make noise. Accordingly, the pump unit (102) may employ a backpressure device in the form of a leaf spring (not shown) that is placed over the outlet of the pump (103) to reduce the noise emanating from the pump check valves.

Flow Measurement Alternatives

Figure 7:
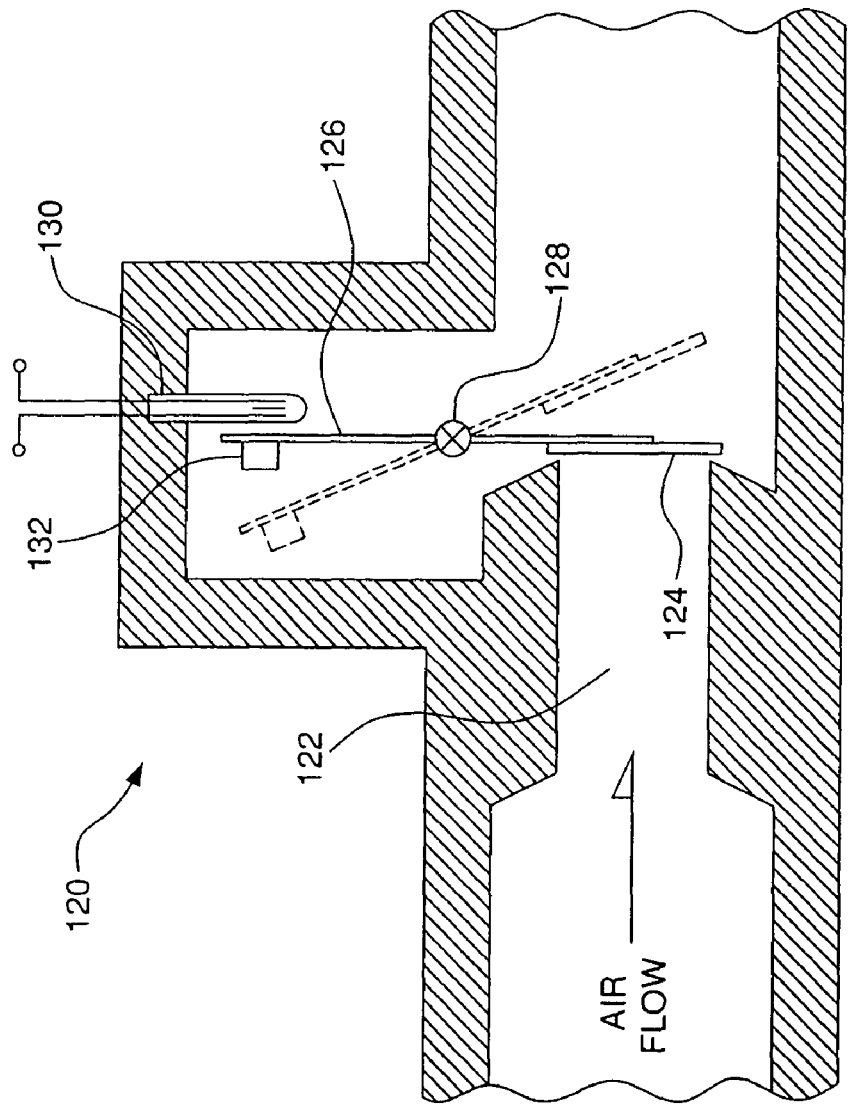
FIG. 7 is a schematic view of an alternate flow monitor using a target meter.

There are other devices for determining the flow through the system that could be employed as leak detection devices in a wound dressing system operating with a reference airflow. These devices measure flow directly, and thus can be used with non-positive displacement pumps and wall vacuum sources as well as with positive displacement pumps. As shown in FIG. 7, a target meter (120) is a reliable device for flow detection that is insensitive to changes in pressure. The target meter (120) employs an inlet orifice (122) and a target (124) typically placed in close proximity to the orifice. The target is attached to a shaft (126) and pivots on points (128) or an armature. A light torsion spring (not shown) may be used to keep the target in close proximity to the orifice. The extension of the shaft is placed outside of the flow path. As flow enters the orifice, the target is forced away from the orifice. A proximity sensor, such as a reed switch (130) is so placed as to detect the positions of a magnet (132) on the end of the shaft extension and thus the presence or absence of flow in the circuit as well as measuring flow rate. A target meter could be placed between the waste collection canister and the pump or at the outlet of the pump, or between the waste collection canister and a stationary suction source to provide analogous flow rate information as previously described.

Other flow detection devices that could be used alone or in conjunction with a suction source include a hot wire anemometer that determines flow as a function of the cooling of a wire in a flowing air stream, a rotameter with an optical detector that senses the position of a float, a turbine meter that rotates when flow is applied. These flow detection systems are generally insensitive to changes in pressure. A hot wire anemometer could be placed between the waste collector (16) and the pump (103) or at the inlet of the pump (103), or between the waste collector (16) and or a stationary suction source. These alternative flow sensors allow the use of other styles of pumps that are not positive displacement, such as vane pumps and scroll pumps. Almost any flow instrument could be used, including, for example, differential pressure (DP) cells that provide an indirect measure of flow rate.

When any fault condition is determined within the system, the pump (103) will continue to run, delivering a sub-optimal level of suction, until the condition is corrected or the user powers the system off, since a sub-optimum level of suction applied to the wound is preferable to no suction at all.

Therapeutic Fluid Delivery and Reference Airflow

Figure 8:
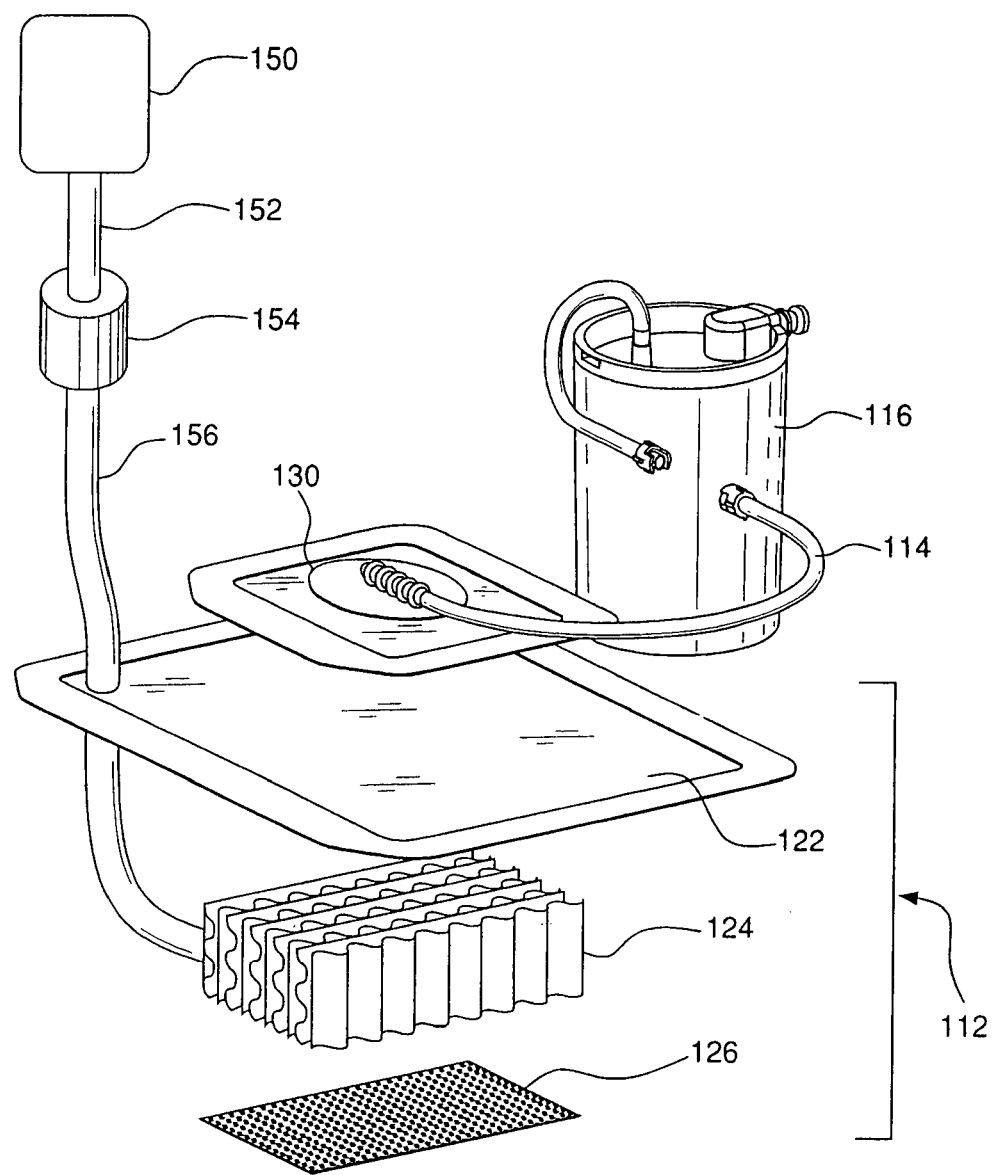
FIG. 8 is an exploded perspective view of a portion of an alternate embodiment of a system for negative pressure wound therapy including therapeutic fluid delivery to the wound.

In the embodiments described above, the reference airflow for discerning between normal and abnormal operation has been ambient air supplied to the suction conduit through a vent. A reference airflow could be provided, however, in the form of a therapeutic mixture, such as oxygen enriched air, nitric oxide, heated humidified air or an aerosol containing medication droplets or particles. Such a configuration is shown in FIG. 8. A source of therapeutic mixture (150), such as an oxygen regulator or a nebulizer, is connected to a conduit (152) leading to the wound. The mixture is conveyed through the conduit under or through the wound cover (122) and released into the wound packing (124) adjacent the wound contact material (126). Part of this mixture will be absorbed, but enough could be returned through the suction conduit (114) to provide a reference airflow when the flow has settled into equilibrium.

While a flow monitor (210) could be associated with a portable pump unit (102) or in front of the appliance fitting of a suction regulator (20), as described above, an airflow monitor (154) could be provided between the therapeutic mixture source (150) and the wound cover (122). Since the part of the conduit beneath the cover would be contaminated in use, a detachable disposable tube (156) would be used for the section of conduit from the monitor (154) to the wound packing (112). Thus, the invention can provide for the maintenance of suction therapy on a wound as well as the ability to monitor the application and removal of therapeutic substances to the wound.

Although the invention has been described and illustrated with respect to several embodiments described above, it should be understood the invention may be embodied in other forms without departing from its scope or attributes. Hence, the scope of the invention should be derived from the claims that follow, recognizing that the claim language may literally encompass structure not specifically described.

We claim:

1. A system for applying negative pressure therapy to a wound, comprising:
    a wound dressing including a wound cover that is sealable to skin surrounding a wound;
    a portable suction pump powered by a battery or by an alternating current electrical power supply;
    a conduit having an end operatively associated with the wound dressing and an opposite end operatively associated with the suction pump, to communicate suction to the wound;
    the suction pump comprising a flow monitor to detect a flow rate in the conduit;
    a waste collector disposed in the conduit between the wound dressing and the suction pump for collecting liquids aspirated from the wound, the waste collector being releasably supported by a docking station on the pump;
    the flow monitor comprising a non-numerical annunciator having an indicator that provides color-coded visual indications of flow conditions including an indication that the flowrate is within a range indicative of a blockage showing an occlusion in the system, normal operation, an indication that the flow rate is at a first level indicative of a first level of leakage in the system, and an indication that the flow rate is at a second level indicative of a second and higher level of leakage in the system.

2. A system as in claim 1, further comprising:
    a pressure transducer for sensing pressure in the system; and
    a pressure controller for controlling the pump to maintain the system pressure between an upper limit and a lower limit around a pressure setpoint.

3. A system as in claim 1, further including an error indicator for displaying a visual warning of one or more system errors, wherein the system errors are chosen from the group consisting of: overpressure detected by the pressure transducer, pressure transducer failure, waste collection canister not attached, low battery voltage, attachment of incorrect power supply, low operating time remaining, collection canister full, and pump motor not operational.

4. A system as in claim 1, wherein the flow monitor detects whether or not the flow rate in the conduit deviates from a range about a reference airflow rate.

5. A system as in claim 4, the pump further including a sensor for determining the level of waste in the collector and the flow monitor further comprising the non-numerical annunciator capable of providing visual indications of flow conditions including that the flow rate is within the reference airflow rate range so as to indicate normal operation, that the flow rate is at a first level above the reference flow rate range so as to indicate a first level of leakage in the system, that the flow rate is at a second level above the reference flow rate range so as to indicate a second higher level of leakage in the system, the second level being a greater deviation from the reference airflow rate than the first level, or that the waste collector is full.

6. A system as in claim 1, further including an error indicator for displaying a visual warning of one or more system errors, wherein the system errors are chosen from the group consisting of: overpressure detected by the pressure transducer, pressure transducer failure, waste collection canister not attached, low battery voltage, attachment of incorrect power supply, low operating time remaining, collection canister full, and pump motor not operational.

7. A system for applying negative pressure therapy to a wound, comprising:
   a wound dressing including a wound cover that is sealable to skin surrounding a wound;
   a conduit having an end operatively associated with the wound dressing and an opposite end operatively associated with a suction source, to communicate suction to the wound;
   a waste collector disposed in the conduit between the wound dressing and the suction source for collecting liquids aspirated from the wound;
   a flow monitor to monitor flow of system fluid in the conduit from the wound dressing to the suction source, wherein the flow monitor comprises a non-numerical annunciator having an indicator that provides color-coded visual indications of flow conditions including an indication that the flow rate is within a range indicative of a blockage showing an occlusion in the system, normal operation, an indication that the flow rate is at a first level indicative of a first level of leakage in the system, and an indication that the flow rate is at a second level indicative of a second and higher level of leakage in the system; and
   an air filter/dryer dehumidifier having an air-impermeable, water vapor-permeable membrane disposed between the waste collector and the flow monitor for removing humidity from the system fluid.

8. A system for applying negative pressure therapy to a wound, comprising:
   a wound dressing including a wound cover that is sealable to skin surrounding a wound;
   a conduit having an end operatively associated with the wound dressing and an opposite end operatively associated with a suction source, to communicate suction to the wound;
   a waste collector disposed in the conduit between the wound dressing and the suction source for collecting liquids aspirated from the wound;
   a flow monitor to monitor flow of system fluid in the conduit from the wound dressing to the suction source, wherein the flow monitor comprises a non-numerical annunciator having an indicator that provides color-coded visual indications of flow conditions including an indication that the flow rate is within a range indicative of a blockage showing an occlusion in the system, normal operation, an indication that the flow rate is at a first level indicative of a first level of leakage in the system, and an indication that the flow rate is at a second level indicative of a second and higher level of leakage in the system; and
   a dehumidifier disposed between the waste collector and the flow monitor for removing humidity from the system fluid wherein the dehumidifier comprises an air-impermeable, water vapor-permeable membrane such that when higher humidity system fluid passes across a side of the membrane and lower humidity ambient air passes across an opposite side of the membrane, water vapor is transported through the membrane from the system fluid to the ambient air.

9. A system as in claim 8, wherein the suction source causes the ambient air to pass across the membrane.

* * * * *